United States Patent
Aoki et al.

(10) Patent No.: US 9,903,833 B2
(45) Date of Patent: Feb. 27, 2018

(54) CONTROL DEVICE AND CONTROL METHOD FOR INTERNAL COMBUSTION ENGINE

(71) Applicant: TOYOTA JIDOSHA KABUSHIKI KAISHA, Toyota-shi, Aichi-ken (JP)

(72) Inventors: Keiichiro Aoki, Shizuoka-ken (JP); Tatsuhiro Hashida, Shizuoka-ken (JP)

(73) Assignee: TOYOTA JIDOSHA KABUSHIKI KAISHA, Toyota-shi, Aichi-ken (JP)

( * ) Notice: Subject to any disclaimer, the term of this patent is extended or adjusted under 35 U.S.C. 154(b) by 82 days.

(21) Appl. No.: 14/913,580

(22) PCT Filed: Aug. 14, 2014

(86) PCT No.: PCT/IB2014/001517
§ 371 (c)(1),
(2) Date: Feb. 22, 2016

(87) PCT Pub. No.: WO2015/025205
PCT Pub. Date: Feb. 26, 2015

(65) Prior Publication Data
US 2016/0209353 A1    Jul. 21, 2016

(30) Foreign Application Priority Data
Aug. 23, 2013    (JP) .................................. 2013-173208

(51) Int. Cl.
| | | |
|---|---|---|
| G01N 27/406 | (2006.01) |
| G01N 27/407 | (2006.01) |
| G01N 27/409 | (2006.01) |
| G01N 33/00 | (2006.01) |

(52) U.S. Cl.
CPC ....... *G01N 27/4067* (2013.01); *G01N 27/409* (2013.01); *G01N 27/4065* (2013.01); *G01N 27/4074* (2013.01); *G01N 33/0036* (2013.01)

(58) Field of Classification Search
CPC ........... G01N 27/4067; G01N 27/4065; G01N 27/409; G01N 27/4074; G01N 33/0036;
(Continued)

(56) References Cited

U.S. PATENT DOCUMENTS

| | | |
|---|---|---|
| 5,145,566 A | 9/1992 | Logothetis et al. |
| 6,051,123 A | 4/2000 | Joshi et al. |

(Continued)

FOREIGN PATENT DOCUMENTS

| | | |
|---|---|---|
| CN | 101548075 A | 9/2009 |
| JP | H02-122255 A | 5/1990 |

(Continued)

OTHER PUBLICATIONS

G. Jasinski, et al., "Lisicon solid electrolyte electrocatalytic gas sensor", Journal of the European Ceramic Society, vol. 25, No. 12, Jan. 1, 2005 (Jan. 1, 2005), pp. 2969-2972, Elsevier Science Publishers, Barking, Essex, GB (XP027618581, ISSN: 0955-2219 [retrieved on Jan. 1, 2005]).

(Continued)

*Primary Examiner* — J. Christopher Ball
(74) *Attorney, Agent, or Firm* — Andrews Kurth Kenyon LLP

(57) ABSTRACT

A control device calculates an SOx concentration in exhaust gas on the basis of a sensor output current when a voltage applied to a limiting current sensor is stepped down from a predetermined voltage value. The control device is configured to step up the voltage applied to the limiting current sensor to the predetermined voltage value when the temperature of the limiting current sensor is equal to or lower than a first predetermined temperature or when a condition in which the temperature of the limiting current sensor is predicted to be equal to or lower than the first predetermined temperature is established.

12 Claims, 15 Drawing Sheets

(58) Field of Classification Search
CPC ............ F01N 9/00; F01N 9/005; F01N 11/00–11/007; F01N 2560/02; F01N 2560/20; F01N 2900/00–2900/06
See application file for complete search history.

(56) References Cited

U.S. PATENT DOCUMENTS

| | | |
|---|---|---|
| 2003/0164023 A1 | 9/2003 | Gruenwald et al. |
| 2008/0140301 A1 | 6/2008 | Ding et al. |
| 2009/0320450 A1 | 12/2009 | Hirota et al. |
| 2014/0116031 A1 | 5/2014 | Yoshida et al. |

FOREIGN PATENT DOCUMENTS

| | | |
|---|---|---|
| JP | H03-100454 A | 4/1991 |
| JP | H10-73561 | 3/1998 |
| JP | 2003-083152 A | 3/2003 |
| JP | 2003-247976 A | 9/2003 |
| JP | 2004-205357 A | 7/2004 |
| JP | 2004-519694 A | 7/2004 |
| JP | 2010-145133 A | 7/2010 |
| JP | 2015-017931 A | 1/2015 |
| JP | 2015-017932 A | 1/2015 |
| WO | 2013-021703 A1 | 2/2013 |
| WO | 2015/004846 A1 | 1/2015 |

OTHER PUBLICATIONS

Grzegorz Jasinski, et al., "Properties of a lithium solid electrolyte gas sensor based on reaction kinetics", Measurement Science and Technology, IOP, vol. 17, No. 1, Jan. 1, 2006 (Jan. 1, 2006), pp. 17-21, Bristol, GB (XP020103335, ISSN: 0957-0233, DOI: 10.1088/0957-0233/17/1/004).

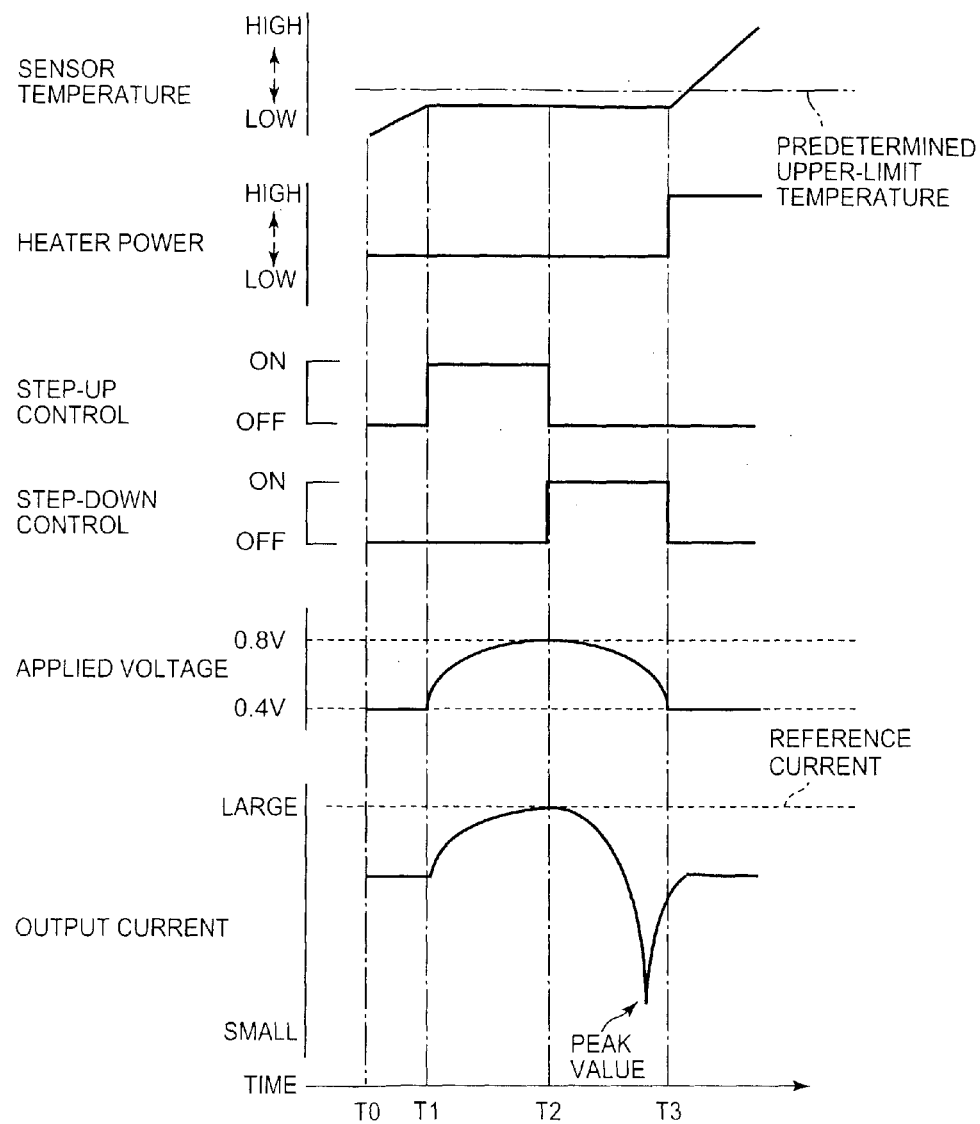

CONTROL DEVICE AND CONTROL METHOD FOR INTERNAL COMBUSTION ENGINE

CROSS-REFERENCE TO RELATED APPLICATIONS

This is a national phase application based on the PCT International Patent Application No. PCT/IB2014/001517 filed Aug. 14, 2014, claiming priority to Japanese Patent Application No. 2013-173208 filed Aug. 23, 2013, the entire contents of both of which are incorporated herein by reference.

BACKGROUND OF THE INVENTION

1. Field of the Invention

The present invention relates to a control device and a control method for an internal combustion engine.

2. Description of Related Art

Japanese Patent Application Publication No. 2-122255 (JP 2-122255 A) discloses a method and a device for measuring a relative amount of one type of oxygen-containing gas in a gas mixture including two types of oxygen-containing gas. Here, the relative amount of oxygen-containing gas (for example, water vapor or carbon dioxide) in the gas is measured by controlling a voltage applied to a cell.

SUMMARY OF THE INVENTION

In the field of internal combustion engines, it may be necessary to detect an SOx concentration (that is, a concentration of sulfur oxide) in exhaust gas. It may also be necessary to calculate a parameter related to SOx (hereinafter referred to as the "SOx-relevant parameter") in the exhaust gas. In this case, it is preferable that it be possible to accurately calculate the SOx-relevant parameter.

The present invention provides a technique of accurately calculating an SOx-relevant parameter in exhaust gas.

A first aspect of the present invention relates to a control device for an internal combustion engine including a limiting current sensor, the control device including an electronic control unit. The electronic control unit is configured to step up a voltage applied to the limiting current sensor to a predetermined voltage when one of follows conditions is satisfied, a temperature of the limiting current sensor is equal to or lower than a first predetermined temperature and a condition in which the temperature of the limiting current sensor is predicted to be equal to or lower than the first predetermined temperature is established. The electronic control unit is configured to calculate a parameter related to SOx in a target gas on the basis of an output current of the limiting current sensor when the voltage applied to the limiting current sensor is stepped down from the predetermined voltage.

According to this configuration, the sensor temperature in a step-up control (in a control of stepping up the voltage applied to the limiting current sensor to the predetermined voltage) is lower than the sensor temperature when the step-up control is not performed. When the sensor temperature in the step-up control is low, SOx (particularly, sulfur components) attached to the sensor in the step-up control is not detached from the sensor. Alternatively, at least detachment of SOx attached to the sensor from the sensor is suppressed. As a result, the output current of the sensor in a step-down control (in a control of stepping down the voltage applied to the limiting current sensor from the predetermined voltage) which is performed after the step-up control exactly corresponds to the amount of SOx. Accordingly, it is possible to accurately calculate an SOx-relevant parameter.

The sensor temperature may include a parameter correlated with the temperature of the sensor and a parameter substantially indicating the temperature of the sensor in addition to the temperature of the sensor itself.

The condition may be a condition in which an engine operating state is a low-load and low-speed operating state or a condition in which the sensor temperature is controlled to be equal to or lower than a first predetermined temperature for the purpose other than the step-up control.

In the aspect, the electronic control unit may be configured to control such that one of the conditions is satisfied, in the course of warming the limiting current sensor up. In the course of warming the sensor up, there is a period in which the sensor temperature is equal to or lower than the first predetermined temperature. At this time, when the sensor temperature is controlled to be equal to or lower than the first predetermined temperature or the condition is established, it is not necessary to actively lower the sensor temperature (or the degree by which the sensor temperature is lowered is small). Therefore, it is possible to efficiently control the sensor temperature to be equal to or lower than the first predetermined temperature. Accordingly, it is possible to efficiently and accurately calculate the SOx-relevant parameter.

In the aspect, the electronic control unit may be configured to give an alarm notifying that a fuel property is abnormal when the absolute value of the output current while stepping down the voltage applied to the limiting current sensor from the predetermined voltage is equal to or greater than a first determination value. According to this configuration, when there is a possibility that the fuel property is abnormal, the possibility that the fuel property is abnormal can be notified. In this case, it is not necessary to clearly calculate the SOx-relevant parameter. In this case, it can be said that a parameter for determining whether an alarm notifying that the fuel property is abnormal is necessary is calculated as the SOx-relevant parameter.

In the aspect, the electronic control unit may be configured to step up the voltage applied to the limiting current sensor to the predetermined voltage when the temperature of the limiting current sensor is equal to or higher than a second predetermined temperature and is equal to or lower than the first predetermined temperature. The second predetermined temperature may be lower than the first predetermined temperature. When the sensor temperature in the step-up control is excessively low, attachment of SOx (particularly, sulfur component) to the sensor in the step-up control may not progress. Therefore, by performing the step-up control only when the sensor temperature is equal to or higher than the second predetermined temperature and equal to or lower than the first predetermined temperature, the attachment of SOx to the sensor in the step-up control progresses. Accordingly, it is possible to further accurately calculate the SOx-relevant parameter.

In the aspect, the electronic control unit may be configured to step up the voltage applied to the limiting current sensor to the predetermined voltage when an oxygen concentration in the target gas is equal to or higher than a predetermined concentration. When the oxygen concentration in the target gas in the step-up control is high, SOx attached to the sensor in the step-up control can be easily detached from the sensor. Therefore, in consideration of accurate calculation of the SOx-relevant parameter, it is necessary to suppress detachment of SOx from the sensor, particularly when the oxygen concentration in the target gas in the step-up control is high. Accordingly, by performing the step-up control only when the oxygen concentration in the target gas is equal to or higher than a predetermined concentration, the step-up control is performed only when it is particularly necessary to suppress the detachment of SOx from the sensor. As a result, it is possible to further efficiently and accurately calculate the SOx-relevant parameter.

In the aspect, the electronic control unit may be configured to step up the voltage applied to the limiting current sensor to the predetermined voltage after a process of reducing sulfur poisoning of the limiting current sensor ends. According to this configuration, the sensor is not poisoned with sulfur at the time of calculating the SOx-relevant parameter. Accordingly, it is possible to further accurately calculate the SOx-relevant parameter.

In the aspect, the limiting current sensor may detect an oxygen concentration in the target gas, and the first predetermined temperature may be set to a temperature lower than a lower-limit temperature of the limiting current sensor suitable for detecting the oxygen concentration by the use of the limiting current sensor when the electronic control unit steps up the voltage applied to the limiting current sensor to the predetermined voltage. The sensor temperature at which the detachment of SOx from the sensor is suppressed is lower than the lower limit value of the sensor temperature suitable for detecting the oxygen temperature by the use of the sensor. Therefore, by setting the first predetermined temperature to a temperature lower than the lower limit value of the sensor temperature suitable for detecting the oxygen concentration by the use of the sensor, it is possible to further satisfactorily suppress detachment of SOx from the sensor. Accordingly, it is possible to further accurately calculate the SOx-relevant parameter. The oxygen concentration is, for example, the concentration of oxygen contained in the target gas when the target gas arrives at the sensor, or the concentration of oxygen produced from NOx in the target gas in the sensor.

In the aspect, when a plurality of the parameters are calculated, the electronic control unit may be configured to set the parameter calculated when the temperature of the limiting current sensor is a lower temperature as a final parameter related to SOx. As described above, when the sensor temperature is excessively low, it is not possible to accurately calculate the SOx-relevant parameter. Therefore, when the sensor temperature is not excessively low, the output current in the step-down control more accurately corresponds to the amount of SOx as the sensor temperature becomes lower. Accordingly, by employing the SOx-relevant parameter calculated when the sensor temperature is at a lower temperature as the final SOx-relevant parameter, it is possible to more accurately calculate the SOx-relevant parameter. Particularly, this idea is useful when the sensor temperature in the step-up control differs whenever performing the step-up control (particularly, when the step-up control is performed when the sensor temperature becomes equal to or lower than the first predetermined temperature instead of actively controlling the sensor temperature to be equal to or lower than the first predetermined temperature).

The SOx-relevant parameter may be an SOx concentration or a coefficient used to control the internal combustion engine, or may be a coefficient set depending on the SOx concentration.

In the aspect, the electronic control unit may be configured to perform a control of reducing the sulfur poisoning of the limiting current sensor when the output current is equal to or larger than a second determination value, while stepping down the voltage applied to the limiting current sensor from the predetermined voltage. According to this configuration, when there is a possibility that the sensor is poisoned with sulfur, it is possible to reduce the sulfur poisoning of the sensor. In this case, it can be said that a parameter for determining whether the sulfur poisoning reducing control is necessary is calculated as the SOx-relevant parameter.

In the aspect, the predetermined voltage may be, for example, equal to or higher than 0.8 V. According to this configuration, it is possible to output the output current accurately corresponding to the amount of SOx from the sensor in the step-down control. Accordingly, it is possible to accurately calculate the SOx-relevant parameter.

In the aspect, the applied voltage at the time of ending of stepping down the voltage applied to the limiting current sensor from the predetermined voltage may be, for example, equal to or lower than 0.7 V. According to this configuration, it is possible to output the output current accurately corresponding to the amount of SOx from the sensor in the step-down control. Accordingly, it is possible to accurately calculate the SOx-relevant parameter.

In the aspect, the electronic control unit may apply a second voltage lower than the predetermined voltage to the limiting current sensor, and the electronic control unit may detect the oxygen concentration in the target gas using the output current of the limiting current sensor when the second voltage is applied to the limiting current sensor. According to this configuration, it is possible to detect the oxygen concentration in the target gas.

In the aspect, the electronic control unit may use a peak value of the output current in the step-down control as the output current for calculating the parameter. The peak value may be the smallest output current (or the largest output current) out of the output current of the step-down control. Therefore, it can be said that the peak value is the output current accurately corresponding to the SOx-relevant parameter. Accordingly, by using the peak value as the output current for calculating the SOx-relevant parameter, it is possible to more accurately calculate the SOx-relevant parameter.

A second aspect of the present invention relates to a control method for an internal combustion engine including a limiting current sensor, the control method being executed by an electronic control unit. The control method includes stepping up, by the electronic control unit, a voltage applied to the limiting current sensor to a predetermined voltage when one of follows conditions is satisfied, a temperature of the limiting current sensor is equal to or lower than a first predetermined temperature and a condition in which the temperature of the limiting current sensor is predicted to be equal to or lower than the first predetermined temperature is established. The control method includes calculating, by the electronic control unit, a parameter related to SOx in a target gas on the basis of an output current of the limiting current sensor when the voltage applied to the limiting current sensor is stepped down from the predetermined voltage.

According to this configuration, the sensor temperature in a step-up control (in a control of stepping up the voltage applied to the limiting current sensor to the predetermined voltage) is low. When the sensor temperature in the step-up control is low, SOx (particularly, sulfur components) attached to the sensor in the step-up control is not detached from the sensor (or, at least detachment of SOx attached to the sensor from the sensor is suppressed). As a result, the output current of the sensor in a step-down control (in a control of stepping down the voltage applied to the limiting current sensor from the predetermined voltage) which is performed after the step-up control exactly corresponds to the amount of SOx. Accordingly, it is possible to accurately calculate the SOx-relevant parameter.

BRIEF DESCRIPTION OF THE DRAWINGS

Features, advantages, and technical and industrial significance of exemplary embodiments of the invention will be described below with reference to the accompanying drawings, in which like numerals denote like elements, and wherein:

FIG. 8 is a timing chart illustrating a case where an SOx concentration is detected in a first embodiment;

DETAILED DESCRIPTION OF EMBODIMENTS

A control device for an internal combustion engine according to the present invention will be described below with reference to the accompanying drawings. Hereinafter, an embodiment of the present invention will be described in conjunction with an example where exhaust gas discharged from the internal combustion engine is used as a target gas and an SOx concentration is used as an SOx-relevant parameter.

Figure 1:
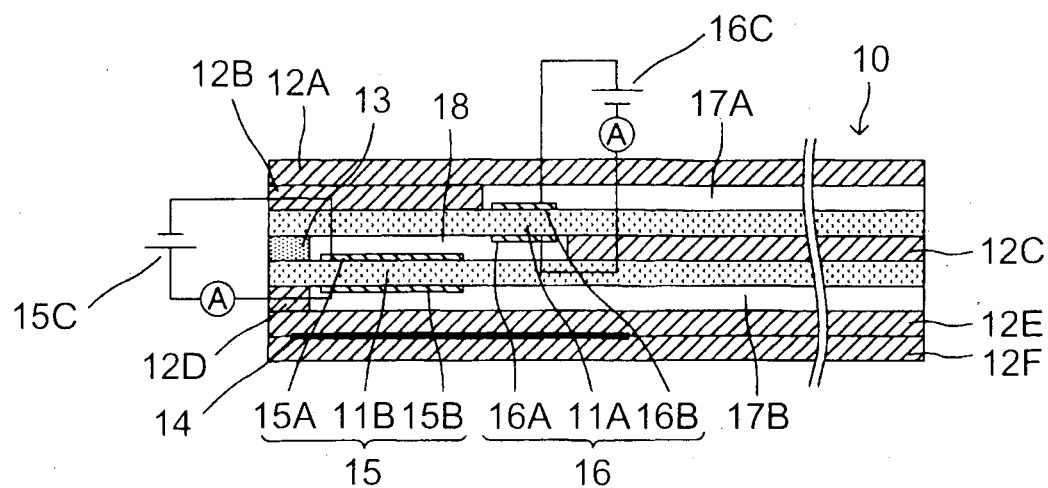
FIG. 1 is a diagram illustrating an example (a two-cell limiting current sensor) of a limiting current sensor according to the present invention.

FIG. 1 illustrates an example of a limiting current sensor according to a first embodiment of the present invention. The limiting current sensor illustrated in FIG. 1 is a two-cell limiting current sensor. In FIG. 1, reference numeral 10 denotes a limiting current sensor, reference numeral 11A denotes a first solid electrolyte layer, reference numeral 11B denotes a second solid electrolyte layer, reference numeral 12A denotes a first alumina layer, reference numeral 12B denotes a second alumina layer, reference numeral 12C denotes a third alumina layer, reference numeral 12D denotes a fourth alumina layer, reference numeral 12E denotes a fifth alumina layer, reference numeral 12F denotes a sixth alumina layer, reference numeral 13 denotes a diffusion-controlling layer, reference numeral 14 denotes a heater, reference numeral 15 denotes a pump cell, reference numeral 15A denotes a first pump electrode, reference numeral 15B denotes a second pump electrode, reference numeral 15C denotes a pump cell voltage source, reference numeral 16 denotes a sensor cell, reference numeral 16A denotes a first sensor electrode, reference numeral 16B denotes a second sensor electrode, reference numeral 16C denotes a sensor cell voltage source, reference numeral 17A denotes a first air introduction passage, reference numeral 17B denotes a second air introduction passage, and reference numeral 18 denotes an internal space.

The solid electrolyte layers 11A, 11B are layers formed of zirconia or the like and has oxygen ion conductivity. The alumina layers 12A to 12F are layers formed of alumina. The diffusion-controlling layer 13 is a porous layer and can transmit exhaust gas. In the limiting current sensor 10, the layers are stacked sequentially from the lower side in FIG. 1 in the order of the sixth alumina layer 12F, the fifth alumina layer 12E, the fourth alumina layer 12D, the second solid electrolyte layer 11B, the diffusion-controlling layer 13, the third alumina layer 12C, the first solid electrolyte layer 11A, the second alumina layer 12B, and the first alumina layer 12A. The heater 14 is disposed between the fifth alumina layer 12E and the sixth alumina layer 12F.

The first air introduction passage 17A is a space formed by the first alumina layer 12A, the second alumina layer 12B, and the first solid electrolyte layer 11A. A part of the first air introduction passage 17A is opened to the atmosphere. The second air introduction passage 17B is a space formed by the second solid electrolyte layer 11B, the fourth alumina layer 12D, and the fifth alumina layer 12E. A part of the second air introduction passage 17B is opened to the atmosphere. The internal space 18 is a space formed by the first solid electrolyte layer 11A, the second solid electrolyte layer 11B, the diffusion-controlling layer 13, and the third alumina layer 12C. A part of the internal space 18 communicates with the outside of the sensor via the diffusion-controlling layer 13.

The first pump electrode 15A and the second pump electrode 15B are electrodes formed of a platinum group element such as platinum or rhodium or an alloy thereof. The first pump electrode 15A is disposed on a wall surface (that is, a wall surface of the second solid electrolyte layer 11B forming the internal space 18) on one side of the second solid electrolyte layer 11B. The second pump electrode 15B is disposed on a wall surface (that is, a wall surface of the second solid electrolyte layer 11B forming the second air introduction passage 17B) on the other side of the second solid electrolyte layer 11B. The first pump electrode 15A, the second pump electrode 15B, and the second solid electrolyte layer 11B constitute the pump cell 15. The limiting current sensor 10 is configured to apply a voltage from the pump cell voltage source 15C to the pump cell 15 (specifically, between the first pump electrode 15A and the second pump electrode 15B). The first pump electrode 15A is an electrode on a negative electrode side. The second pump electrode 15B is an electrode on a positive electrode side.

When a voltage is applied to the pump cell 15 and oxygen in the internal space 18 comes in contact with the first pump electrode 15A, the oxygen becomes oxygen ions on the first pump electrode 15A. The oxygen ions move to the second pump electrode 15B in the second solid electrolyte layer 11B. At this time, a current proportional to the amount of oxygen ions moving in the second solid electrolyte layer 11B flows between the first pump electrode 15A and the second pump electrode 15B. When the oxygen ions reach the second pump electrode 15B, the oxygen ions becomes oxygen on the second pump electrode 15B and the oxygen is discharged to the second air introduction passage 17B. That is, the pump cell 15 can lower the oxygen concentration in exhaust gas by discharging oxygen in the exhaust gas from the exhaust gas by pumping. The pumping capability of the pump cell 15 becomes higher as the voltage applied to the pump cell 15 from the pump cell voltage source 15C becomes higher.

The first sensor electrode 16A and the second sensor electrode 16B are electrodes formed of a platinum group element such as platinum or rhodium or an alloy thereof. The first sensor electrode 16A is disposed on a wall surface (that is, a wall surface of the first solid electrolyte layer 11A forming the internal space 18) on one side of the first solid electrolyte layer 11A. The second sensor electrode 16B is disposed on a wall surface (that is, a wall surface of the first solid electrolyte layer 11A forming the first air introduction passage 17A) on the other side of the first solid electrolyte layer 11A. The first sensor electrode 16A, the second sensor electrode 16B, and the first solid electrolyte layer 11A constitute the sensor cell 16. The limiting current sensor 10 is configured to apply a voltage from the sensor cell voltage source 16C to the sensor cell 16 (specifically, between the first sensor electrode 16A and the second sensor electrode 16B). The first sensor electrode 16A is an electrode on a negative electrode side. The second sensor electrode 16B is an electrode on a positive electrode side.

When a voltage is applied to the sensor cell 16 and SOx in the internal space 18 comes in contact with the first sensor electrode 16A, the SOx is decomposed on the first sensor electrode 16A and the SOx becomes oxygen ions. The oxygen ions move to the second sensor electrode 16B in the first solid electrolyte layer 11A. At this time, a current proportional to the amount of oxygen ions moving in the first solid electrolyte layer 11A flows between the first sensor electrode 16A and the second sensor electrode 16B. When the oxygen ions reach the second sensor electrode 16B, the oxygen ions become oxygen on the second sensor electrode 16B and the oxygen is discharged to the first air introduction passage 17A.

Figure 2:
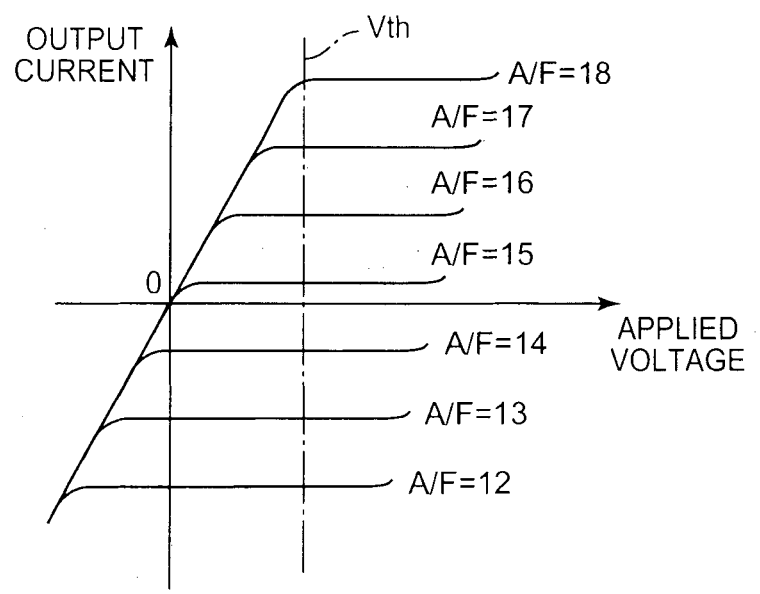
FIG. 2 is a diagram illustrating output characteristics of the limiting current sensor illustrated in FIG. 1.

FIG. 2 illustrates a relationship between a pump cell application voltage and a pump cell output current in the two-cell limiting current sensor of the first embodiment. The pump cell application voltage is a voltage applied to the pump cell 15 from the pump cell voltage source 15C. The pump cell output current is a current flowing between the first pump electrode 15A and the second pump electrode 15B. In FIG. 2, the line indicated by A/F=12 represents a variation of an output current with respect to a variation of the pump cell application voltage when an air-fuel ratio of the exhaust gas is 12. Similarly, the lines indicated by A/F=13 to A/F=18 represent the variation of the output current with respect to the variation of the pump cell application voltage when the air-fuel ratio of the exhaust gas ranges from 13 to 18, respectively.

As illustrated in FIG. 2, for example, when the air-fuel ratio of the exhaust gas is 18 and the pump cell output current has a negative value in a range in which the pump cell application voltage is smaller than a certain value Vth, the higher the pump cell application voltage becomes, the smaller the absolute value of the pump cell output current becomes. When the air-fuel ratio of the exhaust gas is 18 and the pump cell output current has a positive value in a range in which the pump cell application voltage is smaller than the certain value Vth, the higher the pump cell application voltage becomes, the larger the absolute value of the pump cell output current becomes. In a range in which the pump cell application voltage is equal to or higher than the certain value Vth, the pump cell output current is kept constant regardless of the pump cell application voltage.

In this way, the relationship between the pump cell application voltage and the pump cell output current is similarly established when the air-fuel ratio of the exhaust gas is 12 to 17. As can be seen from FIG. 2, when a voltage with which the pump cell output current is kept constant regardless of the pump cell application voltage in the entire range of the air-fuel ratio to be detected is applied to the pump cell 15, it is possible to detect the air-fuel ratio of the exhaust gas on the basis of the pump cell output current detected at that time. That is, the two-cell limiting current sensor 10 of the first embodiment can be used to detect the air-fuel ratio of the exhaust gas. The air-fuel ratio of the exhaust gas is a parameter having a correlation with an oxygen concentration in the exhaust gas. Accordingly, in principle, the two-cell limiting current sensor of the first embodiment can detect the oxygen concentration in the exhaust gas.

A relationship between a sensor cell application voltage and a sensor cell output current in the two-cell limiting current sensor of the first embodiment is the same as illustrated in FIG. 2. Accordingly, in a state where the pump cell application voltage is zero, when a voltage with which the sensor cell output current is kept constant regardless of the sensor cell application voltage in the entire range of the air-fuel ratio to be detected is applied to the sensor cell 16, it is possible to detect the air-fuel ratio of the exhaust gas on the basis of the sensor cell output current detected at that time. The state where the pump cell application voltage is zero is a state where the pump cell 15 is not activated. That is, the two-cell limiting current sensor 10 of the first embodiment can be used to detect the air-fuel ratio of the exhaust gas. The sensor cell application voltage is a voltage which is applied to the sensor cell 16 from the sensor cell voltage source 16C. The sensor cell output current is a current flowing between the first sensor electrode 16A and the second sensor electrode 16B.

It was newly proved through the study of the inventor et al. of the present invention that the current corresponding to the SOx concentration in the exhaust gas could be obtained from the limiting current sensor by lowering the voltage applied to the two-cell limiting current sensor from a predetermined voltage (hereinafter, referred to as "SOx concentration detection voltage"). This will be described below. In the following description, the output current is a current output from the sensor cell 16. Specifically, the voltage applied to the two-cell limiting current sensor is a voltage applied from the sensor cell voltage source 16C to the sensor cell 16.

Figure 3:
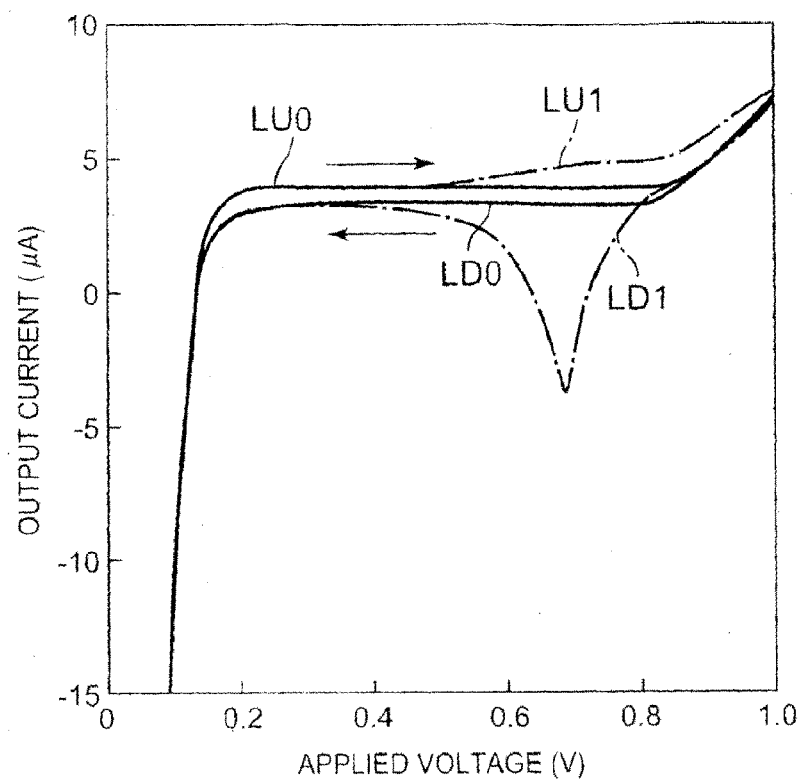
FIG. 3 is a diagram illustrating output characteristics of the limiting current sensor illustrated in FIG. 1.

FIG. 3 illustrates a variation of the output current when the applied voltage gradually increases from 0.1 V to 1.0 V and then gradually decreases from 1.0 V to 0.1 V. The horizontal axis in FIG. 3 represents the applied voltage. The vertical axis in FIG. 3 represents the output current. While the applied voltage is being changed in this way, a voltage with which the oxygen concentration in the exhaust gas in the internal space 18 is set to zero (or substantially zero) is applied to the pump cell 15.

In FIG. 3, the solid line LU0 represents the variation of the output current when SOx is not included in the exhaust gas (that is, the SOx concentration in the exhaust gas is zero) and the applied voltage increases from 0.1 V to 1.0 V. Similarly, the solid line LD0 represents the variation of the output current when SOx is not included in the exhaust gas and the applied voltage decreases from 1.0 V to 0.1 V. In FIG. 3, the alternate long and short dash line LU1 represents the variation of the output current when SOx is included in the exhaust gas and the applied voltage increases from 0.1 V to 1.0 V. Similarly, the alternate long and short dash line LD1 represents the variation of the output current when SOx is included in the exhaust gas and the applied voltage decreases from 1.0 V to 0.1 V.

When SOx is not included in the exhaust gas and the applied voltage increases from 0.1 V to about 0.2 V, the output current rapidly increases to about 4 μA as indicated by the solid line LU0 in FIG. 3. While the applied voltage increases from about 0.2 V to about 0.85 V, the output current is kept substantially constant at about 4 μA. When the applied voltage is higher than about 0.85 V, the output current starts increasing. The output current gradually increases while the applied voltage gradually increases from about 0.85 V to 1.0 V, and the output current reaches about 7 μA when the applied voltage reaches 1.0 V.

Thereafter, when the applied voltage gradually decreases from 1.0 V to 0.4 V, the output current gradually decreases from about 7 μA as indicated by the solid line LD0 in FIG. 3. Unfit the applied voltage decreases to less than about 0.85 and then reaches 0.4 V, the output current is kept substantially constant at about 3.5 μA.

When SOx is included in the exhaust gas and the applied voltage increases from 0.1 V to about 0.2 V, the output current rapidly increases to about 4 μA as indicated by the alternate long and short dash line LU1 in FIG. 3. While the applied voltage increases from about 0.2 V to about 0.6 V, the output current is kept substantially constant at about 4 μA. When the applied voltage is higher than about 0.6 V, the output current starts increasing. The output current gradually increases while the applied voltage increases from about 0.6 V to 1.0 V, and the output current reaches about 7 μA when the applied voltage reaches 1.0 V.

Thereafter, when the applied voltage gradually decreases from 1.0 V to 0.4 V, the output current gradually decreases from about 7 μA as indicated by the alternate long and short dash line LD1 in FIG. 3. Until the applied voltage decreases to less than about 0.8 and then reaches 0.7 V, the output current rapidly decreases, the direction in which the output current flows is reversed, and the output current reaches about 5 μA. While the applied voltage further decreases from about 0.7 V to 0.4 V, the output current rapidly increases and the direction in which the output current flows is returned to the original direction. When the applied voltage reaches 0.4 V, the output current becomes about 3.5 μA.

Therefore, when SOx is included in the exhaust gas and the applied voltage increases from 0.4 V to 0.8 V and then decreases from 0.8 V to 0.4 V, the output current rapidly decreases while the applied voltage decreases, and then rapidly increases. That is, when the applied voltage decreases from 0.8 V to 0.4 V, the output current exhibits a variation having a minimum value (that is, peak value). Here, when the applied voltage reaches about 0.7 V, the output current becomes the peak value.

The output current until the applied voltage is higher than about 0.6 V and then reaches 1.0 V when SOx is included in the exhaust gas is larger than the output current until the applied voltage is higher than about 0.6 V and then reaches 1.0 V when SOx is not included in the exhaust gas.

Figure 4:
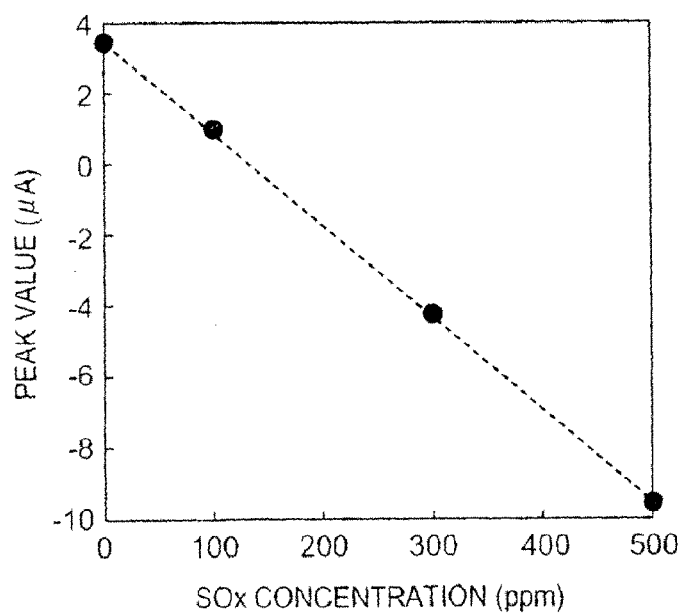
FIG. 4 is a diagram illustrating a relationship between an SOx concentration and a peak value of an output current.

It was proved through the study of the inventor et al. of the present invention that peak value of the output current and the SOx concentration when the applied voltage decreases from 0.8 V to 0.4 V as described above in the two-cell limiting current sensor have the relationship illustrated in FIG. 4. That is, it was proved that the larger the difference between a reference current (that is, the output current when the applied voltage reaches 0.8 V) and the peak value becomes, the higher the SOx concentration in the exhaust gas becomes. In the two-cell limiting current sensor of the first embodiment can be used to detect the oxygen concentration in the exhaust gas (in addition, the air-fuel ratio of the exhaust gas). Accordingly, according to the two-cell limiting current sensor of the first embodiment, it is possible to calculate (that is, detect) the SOx concentration using the peak value by employing the sensor that can be used to detect the oxygen concentration in the exhaust gas.

Figure 5:
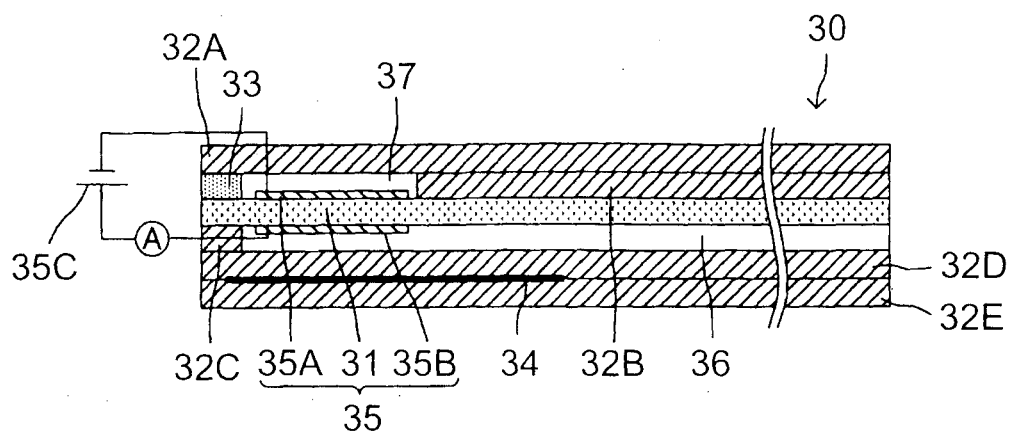
FIG. 5 is a diagram illustrating another example (a one-cell limiting current sensor) of a limiting current sensor according to the present invention.

FIG. 5 illustrates an example of the limiting current sensor of the first embodiment of the present invention. The limiting current sensor illustrated in FIG. 5 is a one-cell limiting current sensor. In FIG. 5, reference numeral 30 denotes a limiting current sensor, reference numeral 31 denotes a solid electrolyte layer, reference numeral 32A denotes a first alumina layer, reference numeral 32B denotes a second alumina layer, reference numeral 32C denotes a third alumina layer, reference numeral 32D denotes a fourth alumina layer, reference numeral 32E denotes a fifth alumina layer, reference numeral 33 denotes a diffusion-controlling layer, reference numeral 34 denotes a heater, reference numeral 35 denotes a sensor cell, reference numeral 35A denotes a first sensor electrode, reference numeral 35B denotes a second sensor electrode, reference numeral 35C denotes a sensor cell voltage source, reference numeral 36 denotes an air introduction passage, and reference numeral 37 denotes an internal space.

The solid electrolyte layer 31 is a layer formed of zirconia or the like and has oxygen ion conductivity. The alumina layers 32A to 32E are layers formed of alumina. The diffusion-controlling layer 33 is a porous layer and can transmit exhaust gas. In the sensor 30, the layers are stacked sequentially from the lower side in FIG. 5 in the order of the fifth alumina layer 32E, the fourth alumina layer 32D, the third alumina layer 32C, the solid electrolyte layer 31, the diffusion-controlling layer 33, the second alumina layer 32B, and the first alumina layer 32A. The heater 34 is disposed between the fourth alumina layer 32D and the fifth alumina layer 32E.

The air introduction passage 36 is a space formed by the solid electrolyte layer 31, the third alumina layer 32C, and the fourth alumina layer 32D. A part of the air introduction passage 36 is opened to the atmosphere. The internal space 37 is a space formed by the first alumina layer 32A, the solid electrolyte layer 31, the diffusion-controlling layer 33, and the second alumina layer 32B. A part of the internal space 37 communicates with the outside of the sensor via the diffusion-controlling layer 33.

The first sensor electrode 35A and the second sensor electrode 35B are electrodes formed of a platinum group element such as platinum or rhodium or an alloy thereof. The first sensor electrode 35A is disposed on a wall surface (that is, a wall surface of the solid electrolyte layer 31 forming the internal space 37) on one side of the solid electrolyte layer 31. The second sensor electrode 35B is disposed on a wall surface (that is, a wall surface of the solid electrolyte layer 31 forming the air introduction passage 36) on the other side of the solid electrolyte layer 31. The first sensor electrode 35A, the second sensor electrode 35B, and the solid electrolyte layer 31 constitute the sensor cell 35. The sensor 30 is configured to apply a voltage from the sensor cell voltage source 35C to the sensor cell 35 (specifically, between the first sensor electrode 35A and the second sensor electrode 35B). The first sensor electrode 35A is an electrode on a negative electrode side. The second sensor electrode 35B is an electrode on a positive electrode side.

When a voltage is applied to the sensor cell 35 and SOx in the internal space 37 comes in contact with the first sensor electrode 35A, the SOx is decomposed on the first sensor electrode 35A and the SOx becomes oxygen ions. The oxygen ions move to the second sensor electrode 35B in the solid electrolyte layer 31. At this time, a current proportional to the amount of oxygen ions moving in the solid electrolyte layer 31 flows between the first sensor electrode 35A and the second sensor electrode 35B. When the oxygen ions reach the second sensor electrode 35B, the oxygen ions become oxygen on the second sensor electrode 35B and the oxygen is discharged to the air introduction passage 36.

A sensor cell application voltage and a sensor cell output current in the one-cell limiting current sensor of the first embodiment is the same relationship as illustrated in FIG. 2. Accordingly, when a voltage with which the sensor cell output current is kept constant regardless of the sensor cell application voltage in the entire range of the air-fuel ratio to be detected is applied to the sensor cell 35, it is possible to detect the air-fuel ratio of the exhaust gas on the basis of the sensor cell output current detected at that time. That is, the one-cell limiting current sensor 30 of the first embodiment can be used to detect the air-fuel ratio of the exhaust gas. The air-fuel ratio of the exhaust gas is a parameter having a correlation with the oxygen concentration in the exhaust gas. Accordingly, in principle, the one-cell limiting current sensor of the first embodiment can detect the oxygen concentration in the exhaust gas. The sensor cell application voltage is a voltage which is applied to the sensor cell 35 from the sensor cell voltage source 35C. The sensor cell output current is a current flowing between the first sensor electrode 35A and the second sensor electrode 35B.

Similarly to the two-cell limiting current sensor, it was proved through the study of the inventor et al. of the present invention that the current corresponding to the SOx concentration in the exhaust gas could be obtained from the limiting current sensor by lowering the voltage applied to the one-cell limiting current sensor from a predetermined voltage (hereinafter, referred to as "SOx concentration detection voltage"). This will be described below. In the following description, the output current is a current output from the sensor cell 35 and the oxygen concentration in the exhaust gas is constant at 1%. Specifically, the voltage applied to the one-cell limiting current sensor is a voltage applied from the sensor cell voltage source 35C to the sensor cell 35.

Figure 6:
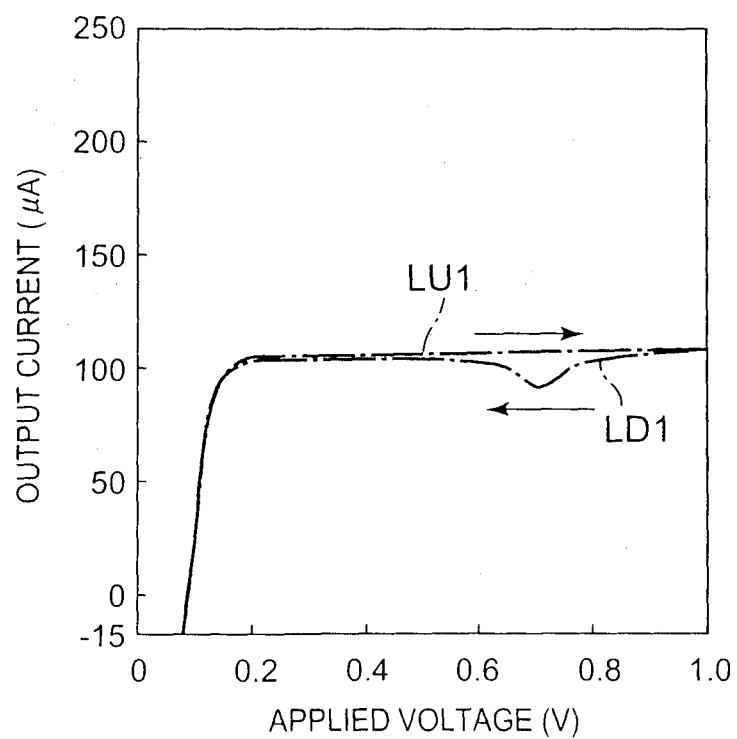
FIG. 6 is a diagram illustrating output characteristics of the limiting current sensor illustrated in FIG. 5.

FIG. 6 illustrates a variation of the output current when the applied voltage gradually increases from 0.1 V to 1.0 V and then gradually decreases from 1.0 V to 0.1 V. The horizontal axis in FIG. 6 represents the applied voltage. The vertical axis in FIG. 6 represents the output current.

In FIG. 6, the alternate long and short dash line LU1 represents the variation of the output current when SOx is included in the exhaust gas and the applied voltage increases from 0.1 V to 1.0 V. Similarly, the alternate long and short dash line LD1 represents the variation of the output current when SOx is included in the exhaust gas and the applied voltage decreases from 1.0 V to 0.1 V.

When SOx is included in the exhaust gas and the applied voltage increases from 0.1 V to about 0.2 V, the output current rapidly increases to about 100 μA as indicated by the alternate long and short dash line LU1 in FIG. 6. While the applied voltage increases from about 0.2 V to about 0.6 V, the output current is kept substantially constant at about 100 μA. When the applied voltage is higher than about 0.6 V, the output current starts increasing. The output current gradually increases while the applied voltage gradually increases from about 0.6 V to 1.0 V, and the output current reaches about 105 μA when the applied voltage reaches 1.0 V.

Thereafter, when the applied voltage gradually decreases from 1.0 V to 0.4 V, the output current gradually decreases from about 105 μA as indicated by the alternate long and short dash line LD1 in FIG. 6. Until the applied voltage decreases to less than about 0.8 and then reaches 0.7 V, the output current rapidly decreases and reaches about 80 μA. While the applied voltage further decreases from about 0.7 V to 0.4 V, the output current rapidly increases. When the applied voltage reaches 0.4 V, the output current becomes about 100 μA.

Therefore, when SOx is included in the exhaust gas and the applied voltage increases from 0.4 V to 0.8 V and then decreases from 0.8 V to 0.4 V, the output current rapidly decreases while the applied voltage decreases, and then rapidly increases. That is, when the applied voltage decreases from 0.8 V to 0.4 V, the output current exhibits a variation having a minimum value (that is, peak value). Here, when the applied voltage reaches about 0.7 V, the output current becomes the peak value.

It was proved through the study of the inventor et al. of the present invention that peak value of the output current and the SOx concentration when the applied voltage decreases from 0.8 V to 0.4 V as described above in the one-cell limiting current sensor have the relationship illustrated in FIG. 4. That is, it was proved that the larger the difference between a reference current (that is, the output current when the applied voltage reaches 0.8 V) and the peak value becomes, the higher the SOx concentration in the exhaust gas becomes. In the one-cell limiting current sensor of the first embodiment can be used to detect the oxygen concentration in the exhaust gas (in addition, the air-fuel ratio of the exhaust gas). Accordingly, according to the one-cell limiting current sensor of the first embodiment, it is possible to calculate (that is, detect) the SOx concentration using the peak value by employing the sensor that can be used to detect the oxygen concentration in the exhaust gas.

Figure 7:
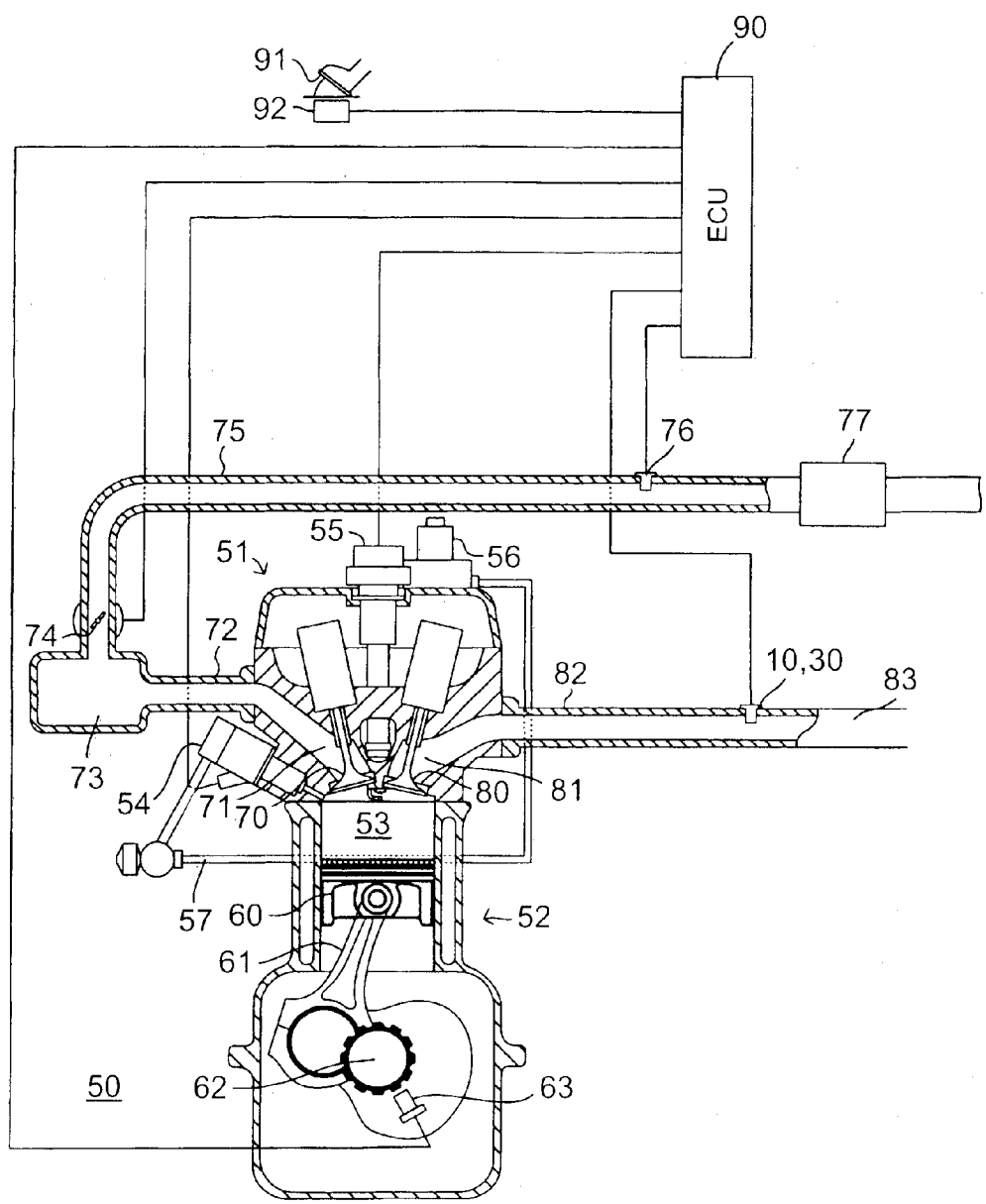
FIG. 7 is a diagram illustrating an internal combustion engine including an SOx concentration detector having the limiting current sensor illustrated in FIG. 1 or 5.

FIG. 7 illustrates an internal combustion engine including an SOx concentration detector having the limiting current sensor 10 illustrated in FIG. 1 or the limiting current sensor 30 illustrated in FIG. 5. The internal combustion engine illustrated in FIG. 7 is a spark-ignited internal combustion engine (a so-called gasoline engine). The present invention may be applied to a compression self-ignition type internal combustion engine (a so-called diesel engine). The internal combustion engine illustrated in FIG. 7 is operated in a state where the air-fuel ratio is a theoretical air-fuel ratio (stoichiometry) in most of an engine operating area.

In FIG. 7, reference numeral 10 or 30 denotes the limiting current sensor illustrated in FIG. 1 or 5, 50 denotes a main body of the internal combustion engine, 51 denotes a cylinder head, 52 denotes a cylinder block, 53 denotes a combustion chamber, 54 denotes a fuel injection valve, 55 denotes an ignition plug, 56 denotes a fuel pump, 57 denotes a fuel supply pipe, 60 denotes a piston, 61 denotes a connecting rod, 62 denotes a crank shaft, 63 denotes a crank angle sensor, 70 denotes an intake valve, 71 denotes an intake port, 72 denotes an intake manifold, 73 denotes a surge tank, 74 denotes a throttle valve, 75 denotes an intake pipe, 76 denotes an air flowmeter, 77 denotes an air filter, 80 denotes an exhaust valve, 81 denotes an exhaust port, 82 denotes an exhaust manifold, 83 denotes an exhaust pipe, 90 denotes an electronic control unit (ECU), 101 denotes an accelerator pedal, and 102 denotes an accelerator pedal pressure sensor.

The fuel injection valve 54, the ignition plug 55, the throttle valve 74, the crank angle sensor 63, the air flowmeter 76, the accelerator pedal pressure sensor 102, and the limiting current sensor 10 or 30 are electrically connected to the ECU 90. The ECU 90 transmits signals for operating the fuel injection valve 54, the ignition plug 55, and the throttle valve 74 thereto. The ECU 90 receives signals from the crank angle sensor 63, the air flowmeter 76, and the accelerator pedal pressure sensor 102. A signal corresponding to the rotation speed of the crank shaft 62 is output from the crank angle sensor 63. The ECU 90 calculates the engine rotation speed on the basis of the signal received from the crank angle sensor 63. A signal corresponding to a flow rate of air (in addition, the flow rate of air suctioned into the combustion chamber 53) passing therethrough is output from the air flowmeter 76. The ECU 90 calculates an amount of air suctioned on the basis of the signal received from the air flowmeter 76. A signal corresponding to the pressure applied to the accelerator pedal 101 is output from the accelerator pedal pressure sensor 102. The ECU 90 calculates an engine load on the basis of the signal received from the accelerator pedal pressure sensor 102.

The limiting current sensor 10 or 30 is attached to the exhaust pipe 83. Accordingly, the gas to be detected by the limiting current sensor 10 or 30 (that is, target gas) is the exhaust gas discharged from the combustion chamber 53. A current corresponding to the SOx concentration in the exhaust gas flowing thereto is output from limiting current sensor 10 or 30. The ECU 90 calculates the SOx concentration on the basis of the current received from the limiting current sensor 10 or 30 (details of this calculation method will be described later).

The detection of an SOx concentration in the first embodiment will be described below. In the following description, a step-up control is a control of increasing the voltage applied to the limiting current sensor 10 or 30 from 0.4 V to 0.8 V in the detection of the SOx concentration. A step-down control is a control of decreasing the voltage applied to the limiting current sensor 10 or 30 from 0.8 V to 0.4 V in the detection of the SOx concentration.

In the first embodiment, the detection of the SOx concentration is performed in the course of warming up the sensor. That is, in the course of warming up the sensor, the step-up control is performed and then the step-down control is performed while controlling a sensor temperature of the limiting current sensor 10 or 30 (that is, the temperature of the sensor, particularly, the temperature of the first sensor electrode) so as to be equal to or lower than a predetermined upper-limit temperature (a first predetermined temperature). At this time, the ECU 90 calculates (that is, detects) the SOx concentration using the peak value of the output current input to the ECU 90 in the step-down control and the reference current. At this time, the larger the difference between the reference current and the peak value becomes, the higher the calculated SOx concentration becomes.

When the SOx concentration is calculated using the difference (hereinafter, referred to as "current difference") between the peak value and the reference current, for example, the SOx concentration corresponding to the current difference is calculated in advance by experiment for each current difference. The calculated SOx concentrations are stored in the ECU 90 in the form of a map of a function of the current difference, and the SOx concentration is calculated by reading the SOx concentration corresponding to the current difference calculated in the course of detection of the SOx concentration from the map.

In the first embodiment, the sensor temperature is controlled so as to be higher than a predetermined upper-limit temperature by performing the step-down control and then performing a high-temperature sensor warming-up control.

The predetermined upper-limit temperature means the highest temperature out of the temperatures at which sulfur components in the exhaust gas attached to the first sensor electrode in the step-up control are not detached from the first sensor electrode. Alternatively, the predetermined upper-limit temperature is the highest temperature out of the temperatures at which the amount or ratio of sulfur components detached from the first sensor electrode out of the sulfur components in the exhaust gas attached to the first sensor electrode in the step-up control is suppressed to be smaller than a predetermined value. Particularly, the predetermined upper-limit temperature is a temperature lower than the oxygen concentration detection temperature. Specifically, the predetermined upper-limit temperature is a temperature lower than 700° C.

The low-temperature sensor warming-up control is a control of warming up the sensor and can be said to be a control of controlling the sensor temperature so as to be equal to or lower than the predetermined upper-limit temperature. The high-temperature sensor warming-up control is a control of warming up the sensor and can be said to be a control of controlling the sensor temperature so as to be higher than the predetermined upper-limit temperature.

The course of warming up the sensor is a period in which the sensor temperature increases to a temperature equal to or higher than the predetermined upper-limit temperature.

In the first embodiment, regardless of whether or not it is necessary to detect the SOx concentration, the step-up control is performed in the course of warming up the sensor while performing the low-temperature sensor warming-up control. When it is necessary to detect the SOx concentration, the step-up control may be performed in the course of warming up the sensor while performing the low-temperature sensor warming-up control.

The SOx concentration detection of the first embodiment will be described below with reference to FIG. 8. In the following description, heater power is power supplied to the heater of the sensor.

In the example illustrated in FIG. 8, at time T0, the internal combustion engine is started. Then, the applied voltage is controlled to 0.4 V and the warming-up of the sensor is started. When the warming-up of the sensor is started, the heater power becomes relatively low power by performing the low-temperature sensor warming-up control and the sensor temperature gradually rises. At time T1, the step-up control is performed. At this time, the sensor temperature is equal to or lower than the predetermined upper-limit temperature. Then, at time T2, the step-up control is ended and the step-down control is performed. When the step-down control is ended, the low-temperature sensor warming-up control is ended and the heater power rises by performing the high-temperature sensor warming-up control. Then, the sensor temperature rises to be higher than the predetermined upper-limit temperature. Here, the ECU 90 calculates (that is, detects) the SOx concentration using the peak value of the output current input to the ECU 90 in the step-down control and the reference current. At this time, the larger the difference between the reference current and the peak value becomes, the higher the calculated SOx concentration becomes.

The limiting current sensor 10 or 30 of the SOx concentration detector in the first embodiment can be used to detect the oxygen concentration in the exhaust gas (in addition, the air-fuel ratio of the exhaust gas). Accordingly, the SOx concentration detector of the first embodiment can detect the SOx concentration in the exhaust gas using the sensor that can be used to detect the oxygen concentration in the exhaust gas. That is, the influence of SOx to the output current when the applied voltage is kept at a constant voltage (for example, 0.4 V) or the influence of SOx to the output current when the applied voltage increases is smaller than the influence of other components (for example, $O_2$ or NOx) to the output current. However, the knowledge that the influence of SOx to the output current when the applied voltage decreases from the parameter detection voltage (for example, 0.8 V) is greater than the influence of other components to the output current was obtained by the inventor et al. of the present invention. Accordingly, the SOx concentration detector of the first embodiment can accurately detect the SOx concentration in the exhaust gas using the sensor that can be used to detect the oxygen concentration in the exhaust gas.

The peak value is an output current which is most different from the output current when the SOx concentration is zero out of the output current when the applied voltage is decreasing. Therefore, the peak value can be said to be the output current accurately corresponding to the SOx concentration. Accordingly, it is possible to further accurately detect the SOx concentration by using the peak value as the output current for detecting the SOx concentration.

In the first embodiment, the voltage applied to the sensor before starting the step-down control is 0.4 V. Therefore, this voltage is lower than 0.8 V which is the applied voltage at the time of starting the step-down control. Accordingly, according to the first embodiment, the power consumed in detecting the SOx concentration can be reduced in comparison with the case where the voltage applied to the sensor before starting the step-down control is 0.8 V.

According to the first embodiment, it is possible to detect the air-fuel ratio of the exhaust gas and the SOx concentration in the exhaust gas using a single sensor.

According to the detection of the SOx concentration in the first embodiment, it is possible to accurately calculate the SOx concentration. The reason thereof will be described below. When the step-up control is performed, the applied voltage increase, thus SOx is decomposed on the first sensor electrode, and the sulfur component in SOx (that is, sulfur component) is attached (or adsorbed) to the first sensor electrode. Here, when the sensor temperature in the step-up control is high, there is a possibility that the sulfur component attached to the first sensor electrode will be detached from the first sensor electrode. When the sulfur component is detached from the first sensor electrode, the output current of the sensor in the step-down control (control of stepping down the applied voltage from 0.8 V to 0.4 V) which is performed after the step-up control is performed does not accurately correspond to the SOx concentration.

On the other hand, when the sensor temperature in the step-up control is low, the sulfur component attached to the first sensor electrode in the step-up control is not detached from the first sensor electrode. Alternatively, at least detachment of the sulfur component, which has been attached to the first sensor electrode, from the first sensor electrode is suppressed. As a result, the output current of the sensor in the step-down control which is performed after the step-up control is performed accurately corresponds to the SOx concentration. Accordingly, according to the SOx concentration detection of the first embodiment, it is possible to accurately calculate the SOx concentration.

In consideration of the above-mentioned advantages of the SOx concentration detection of the first embodiment, SOx can be said to be a component in which the sulfur component of the SOx is attached to the sensor (particularly, the first sensor electrode) in the step-up control and the sulfur component attached to the sensor is not detached from the sensor (or at least detachment of the sulfur component, which has been attached to the sensor, from the sensor is suppressed) when the sensor temperature in the step-up control is low.

in the course of warming up the sensor, there is a period in which the sensor temperature is equal to or lower than the predetermined upper-limit temperature. At this time, when the sensor temperature is controlled to be equal to or lower than the predetermined upper-limit temperature, it is not necessary to actively lower the sensor temperature (or the degree by which the sensor temperature is lowered is small). Therefore, it is possible to efficiently control the sensor temperature to be equal to or lower than the predetermined upper-limit temperature. Accordingly, according to the SOx concentration detection of the first embodiment, it is possible to efficiently and accurately detect the SOx concentration.

Figure 10:
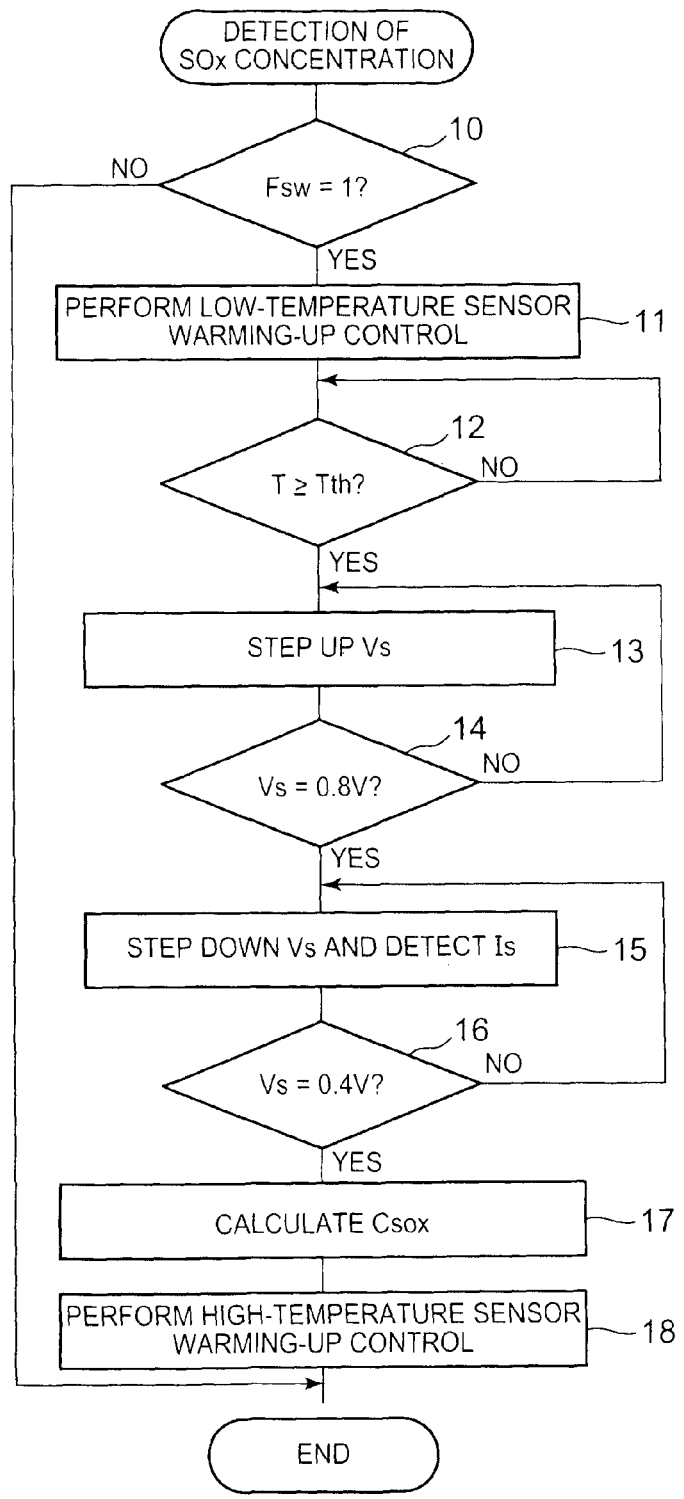
FIG. 10 is a flowchart illustrating an example of an SOx concentration detecting flow in the first embodiment.

An SOx concentration detecting flow in the first embodiment will be described below. An example of this flow is illustrated in FIG. 10. When the flow illustrated in FIG. 10 is started, the applied voltage is kept at 0.4 V. In step 10, it is determined whether or not a sensor warming-up flag Fsw is set (Fsw=1). The sensor warming-up flag Fsw is set when it is necessary to warm up the sensor, and is reset when the warming-up of the sensor is completed. When it is determined in step 10 that Fsw is set to 1, the flow progresses to step 11. On the other hand, when it is determined that Fsw is not set to 1, the flow ends.

In step 11, the low-temperature sensor warming-up control is performed. Subsequently, in step 12, it is determined whether the elapsed time T after the low-temperature sensor warming-up control is started in step 11 is equal to or greater than a predetermined time Tth (T≥Tth). Here, when it is determined that T≥Tth is established, the flow progresses to step 13. On the other hand, when it is determined that T≥Tth is not established, the flow returns to step 12. Accordingly, the progress of the flow to step 13 is on standby until it is determined in step 12 that T≥Tth is established.

In step 13, the applied voltage Vs increases from 0.4 V to 0.8 V. Subsequently, in step 14, it is determined whether the applied voltage Vs reaches 0.8 V (Vs=0.8 V). Here, when it is determined that Vs=0.8 V is established, the flow progresses to step 15. On the other hand, when it is determined that Vs=0.8 V is not established, the flow returns to step 13. Accordingly, until it is determined in step 14 that Vs=0.8 V is established, the applied voltage Vs continues to increase.

In step 15, the applied voltage Vs decreases from 0.8 V to 0.4 V and the output current Is is detected. Subsequently, in step 16, it is determined whether the applied voltage Vs reaches 0.4 V (Vs=0.4 V). Here, when it is determined that Vs=0.4 V is established, the flow progresses to step 17. On the other hand, when it is determined that Vs=0.4 V is not established, the flow returns to step 15. Accordingly, until it is determined in step 16 that Vs=0.4 V is established, the decreasing of the applied voltage Vs and the detecting of the output current Is are continuously performed.

In step 17, the SOx concentration Csox is calculated on the basis of the peak value in the output current Is detected in step 15. Subsequently, in step 18, the high-temperature sensor warming-up control is performed and then the flow ends.

In the SOx concentration detection of the first embodiment, the applied voltage at the time point of starting the step-up control (that is, the applied voltage normally applied to the sensor) is not limited to 0.4 V. The applied voltage at the time point of starting the step-up control only has to be the voltage causing a variation of the output current having a peak value when the applied voltage decreases after the applied voltage increases. The applied voltage at the time point of starting the step-up control is, for example, 0.6 or lower and preferably 0.4 V.

The applied voltage at the time point of ending the step-up control is not limited to 0.8 V. The applied voltage at the time point of ending the step-up control only has to be a voltage causing a variation of the output current having a peak value when the step-down control is performed after the step-up control is performed, or a voltage equal to or higher than the maximum voltage in an output stabilization voltage range, and only has to be, for example, 0.8 V or higher. The output stabilization voltage range is a range in which the output current is substantially constant regardless of the applied voltage when the SOx concentration is zero and is, for example, a range of 0.2 V to 0.8 V.

The applied voltage at the time point of ending the step-down control is not limited to 0.4 V. The applied voltage at the time point of ending the step-down control only has to be equal to or lower than the applied voltage corresponding to the peak value. The applied voltage at the time point of ending the step-down control is, for example, 0.7 V or lower and preferably 0.4 V. Accordingly, the applied voltage at the time point of starting the step-up control may be equal to or different from the applied voltage at the time point of ending the step-down control.

In the SOx concentration detection of the first embodiment, the peak value is used. The output current in a range in which the output current rapidly decreases in the step-down control or a range in which the output current rapidly increases may be used instead of the peak value.

The oxygen concentration in the exhaust gas flowing in the internal space of the sensor may vary with the decrease of the applied voltage. In this case, in consideration that a predetermined time is required for the decrease of the applied voltage, the output current when the applied voltage is 0.4 V can be said to more accurately reflect the oxygen concentration in the exhaust gas in the internal space in the sensor at the time of outputting the peak value than the output current when the applied voltage is 0.8 V. Therefore, in the SOx concentration detection of the first embodiment, when the applied voltage decreases from 0.8 V to 0.4 V, the output current at the time point at which the applied voltage reaches 0.4 V (or the output current after a predetermined time elapses from that time point) may be used instead of the reference current. Accordingly, even when the oxygen concentration in the exhaust gas varies with the decrease of the applied voltage, it is possible to accurately detect the SOx concentration.

In the first embodiment, the SOx concentration may be calculated using the peak value and a conversion coefficient instead of calculating the SOx concentration using the peak value and the reference current. At this time, the larger in the minus direction the peak value becomes, the higher the calculated SOx concentration becomes. The conversion coefficient is a coefficient for converting the peak value into the SOx concentration on the basis of the relationship illustrated in FIG. 4. When the peak value appears as a plus value, the larger in the plus direction the peak value becomes, the higher the calculated SOx concentration becomes.

In the SOx concentration detection of the first embodiment, when the increasing rate or the decreasing rate (sweep speed) of the applied voltage is excessively high, there is a possibility that the peak value will not be output or a possibility that the peak value satisfactorily corresponding to the SOx concentration will not be output in spite of the decrease of the applied voltage. Therefore, in the SOx concentration detection of the first embodiment, it is preferable that the increasing rate and the decreasing rate of the applied voltage with which the peak value satisfactorily corresponding to the SOx concentration is output be selected with the decrease of the applied voltage.

Figure 9A:
FIGS. 9A and 9B are diagrams illustrating an increasing form and a decreasing form of an applied voltage at the time of detecting the SOx concentration.
Figure 9B:

Specifically, as illustrated in FIG. 9A, it is preferable that the applied voltage increase so that the increasing rate of the applied voltage gradually decreases and then the applied voltage decrease so that the decreasing rate of the applied voltage gradually increases. Alternatively, as illustrated in FIG. 9B, it is preferable that the applied voltage increase so that the increasing rate of the applied voltage is kept constant and then the applied voltage decrease so that the decreasing rate of the applied voltage is kept constant.

More specifically, in the SOx concentration detection of the first embodiment, when the variation of the applied voltage until the step-down control is ended after the step-up control is performed is expressed by frequency, this frequency is preferably equal to or lower than 100 Hz. In other words, the time until the step-down control is ended after the step-up control is started is preferably equal to or greater than 0.005 seconds.

The SOx concentration detection of a second embodiment will be described below. Non-configurations and controls out of configurations and controls of several embodiments to be described below are configurations and controls which are the same as the configurations and controls of the embodiments described in this specification or which are obviously derived from the configurations and controls of the embodiments described in this specification.

In the SOx concentration detection of the second embodiment, in the course of warming up the sensor, the step-up control is performed while performing an exhaust gas temperature lowering control.

The exhaust gas temperature lowering control is, for example, a control of performing an engine operation so that the exhaust gas temperature is lowered to such a degree as to lower the sensor temperature to the predetermined upper-limit temperature or lower.

In the second embodiment, in the course of warming up the sensor, the step-up control is performed while performing the exhaust gas temperature lowering control, regardless of whether or not it is necessary to detect the SOx concentration. However, when it is necessary to detect the SOx concentration, the step-up control may be performed in the course of warming up the sensor while performing the exhaust gas temperature lowering control.

In the course of warming up the sensor, there is a period in which the sensor temperature is equal to or lower than the predetermined upper-limit temperature. At this time, when the exhaust gas temperature lowering control is performed, the sensor temperature is likely to be equal to or lower than the predetermined upper-limit temperature. Accordingly, according to the SOx concentration detection of the second embodiment, it is possible to efficiently and accurately detect the SOx concentration.

A third embodiment will be described below. In the third embodiment, a high sensor temperature control of controlling the sensor temperature to be equal to or higher than an oxygen concentration detection temperature is performed. In this case, the warming-up of the sensor means that the sensor temperature is controlled to be equal to or higher than the oxygen concentration detection temperature. In the third embodiment, generally, the applied voltage is normally kept at 0.4 V. That is, 0.4 V is normally applied to the sensor cell. Here, the voltage of 0.4 V is the voltage equal to or higher than the voltage Vth illustrated in FIG. 2 and is a voltage with which the sensor cell output current is constant regardless of the sensor cell application voltage when the air-fuel ratio of the exhaust gas is constant.

Then, the ECU calculates (that is, detects) the air-fuel ratio (that is, the oxygen concentration in the exhaust gas) from the relationship illustrated in FIG. 2 using the sensor cell output current when 0.4 V is normally applied to the sensor cell. That is, the calculating of the air-fuel ratio is performed. Then, the air-fuel ratio of the gas formed in the combustion chamber is calculated on the basis of the detected air-fuel ratio.

When the two-cell limiting current sensor is used to detect the air-fuel ratio in the first embodiment, the voltage applied to the pump cell 15 for detecting the air-fuel ratio is zero.

The oxygen concentration detection temperature is a sensor temperature required for causing the sensor to output the output current accurately corresponding to the oxygen concentration in the exhaust gas, when the sensor is used to detect the air-fuel ratio. In other words, the oxygen concentration detection temperature is a sensor temperature suitable for detecting the oxygen concentration using the sensor. Specifically, the oxygen concentration detection temperature is, for example, a temperature in a range of 700° C. to 800° C.

The SOx concentration detection of the third embodiment will be described below. As described above, in the third embodiment, the high sensor temperature control of controlling the sensor temperature to be equal to or higher than the oxygen concentration detection temperature is generally performed. Here, in the SOx concentration detection of the third embodiment, when it is necessary to detect the SOx concentration (that is, it is necessary to perform the step-up control), the step-up control is performed while performing a low sensor temperature control of controlling the sensor temperature to be equal to or lower than the predetermined upper-limit temperature. More specifically, when it is necessary to detect the SOx concentration, the step-up control is performed while controlling the operation of the heater so that the sensor temperature is equal to or lower than the predetermined upper-limit temperature.

After the SOx concentration is detected, the sensor temperature is kept at a temperature equal to or higher than the predetermined upper-limit temperature and the sensor cell application voltage is kept at 0.4 V by performing the high sensor temperature control. In this state, the air-fuel ratio is detected.

In the low sensor temperature control of the third embodiment, the sensor temperature may be controlled to be equal to or higher than a predetermined lower-limit temperature (the second predetermined temperature). That is, the sensor temperature in the step-up control may be controlled to be in a predetermined temperature range (that is, a temperature range between the predetermined upper-limit temperature and the predetermined lower-limit temperature.

In this case, it is possible to further satisfactorily and accurately detect the SOx concentration. That is, when the sensor temperature in the step-Up control is excessively low, there is a possibility that attachment of the sulfur component to the sensor in the step-up control will not be made. Therefore, by performing the step-up control while controlling the sensor temperature within the temperature range between the predetermined upper-limit temperature and the predetermined lower-limit temperature, the attachment of the sulfur component to the sensor in the step-up control is satisfactorily made. Accordingly, it is possible to further satisfactorily and accurately detect the SOx concentration.

In consideration of the above-mentioned advantages associated with the predetermined lower-limit temperature, the predetermined lower-limit temperature can be said to be the sensor temperature at which the attachment of the sulfur component to the sensor in the step-up control can be satisfactorily made. Specifically, the predetermined lower-limit temperature is a temperature equal to or higher than 500° C.

The SOx concentration detection of the third embodiment will be described below with reference to FIG. 11. In the following description, an SOx concentration detection request flag is a flag which is set when it is necessary to detect the SOx concentration and which is reset when the SOx concentration detection is completed. The heater power is power supplied to the heater.

Figure 11:
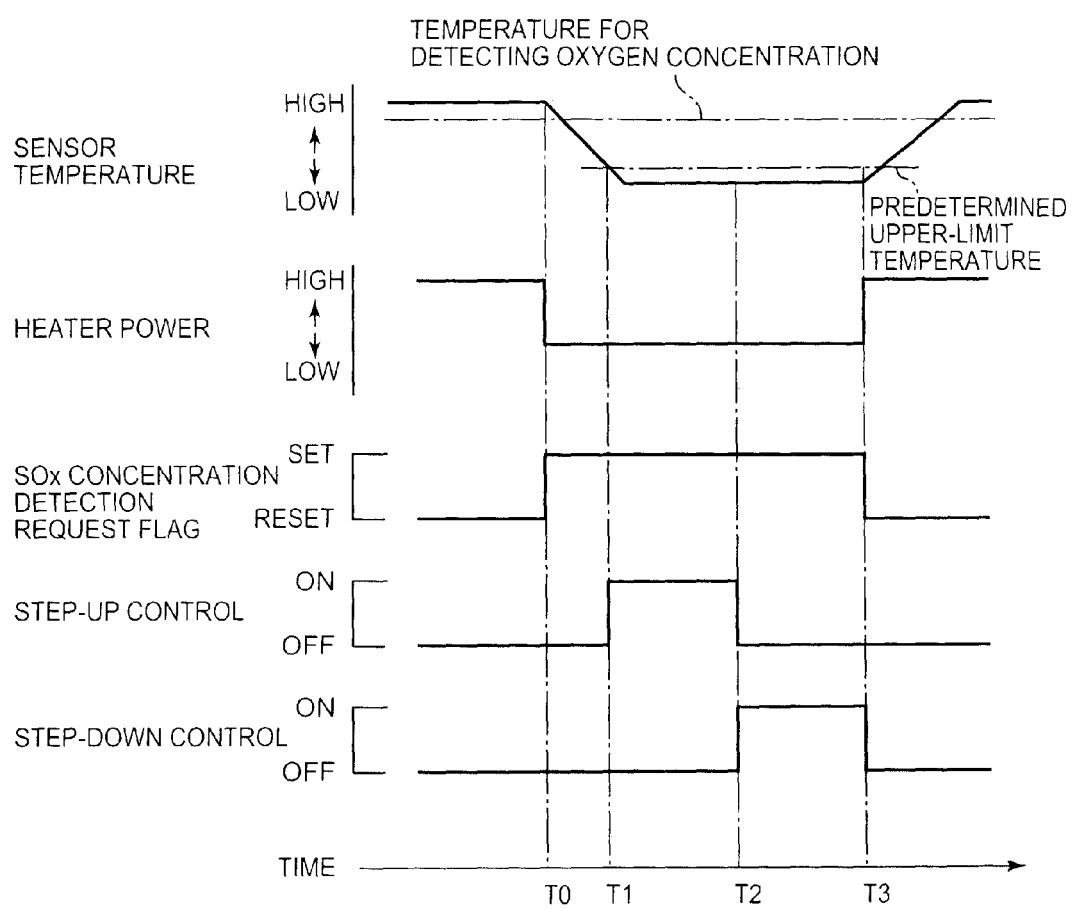
FIG. 11 is a timing chart illustrating a case where an SOx concentration is detected in a third embodiment.

In the example illustrated in FIG. 11, prior to time T0, the sensor temperature is controlled to be equal to or higher than the oxygen concentration detection temperature by performing the high sensor temperature control. At time T0, when the SOx concentration detection request flag is set, the heater power is reduced by performing the low sensor temperature control. Then, the sensor temperature gradually falls. At time T1, when the sensor temperature is equal to or lower than the predetermined upper-limit temperature, the step-up control is performed. At time T2, the step-up control is ended and the step-down control is performed. At time T3, when the step-down control is ended, the heater power increases and is returned to the original power by ending the low sensor temperature control and performing the high sensor temperature control. Then, the sensor temperature rises to be equal to or higher than the oxygen concentration detection temperature.

According to the SOx concentration detection of the third embodiment, for the same reason as described in the first embodiment, it is possible to accurately detect the SOx concentration even when the sensor is warmed up (that is, when the sensor temperature is controlled to be equal to or higher than the oxygen concentration detection temperature).

Figure 12:
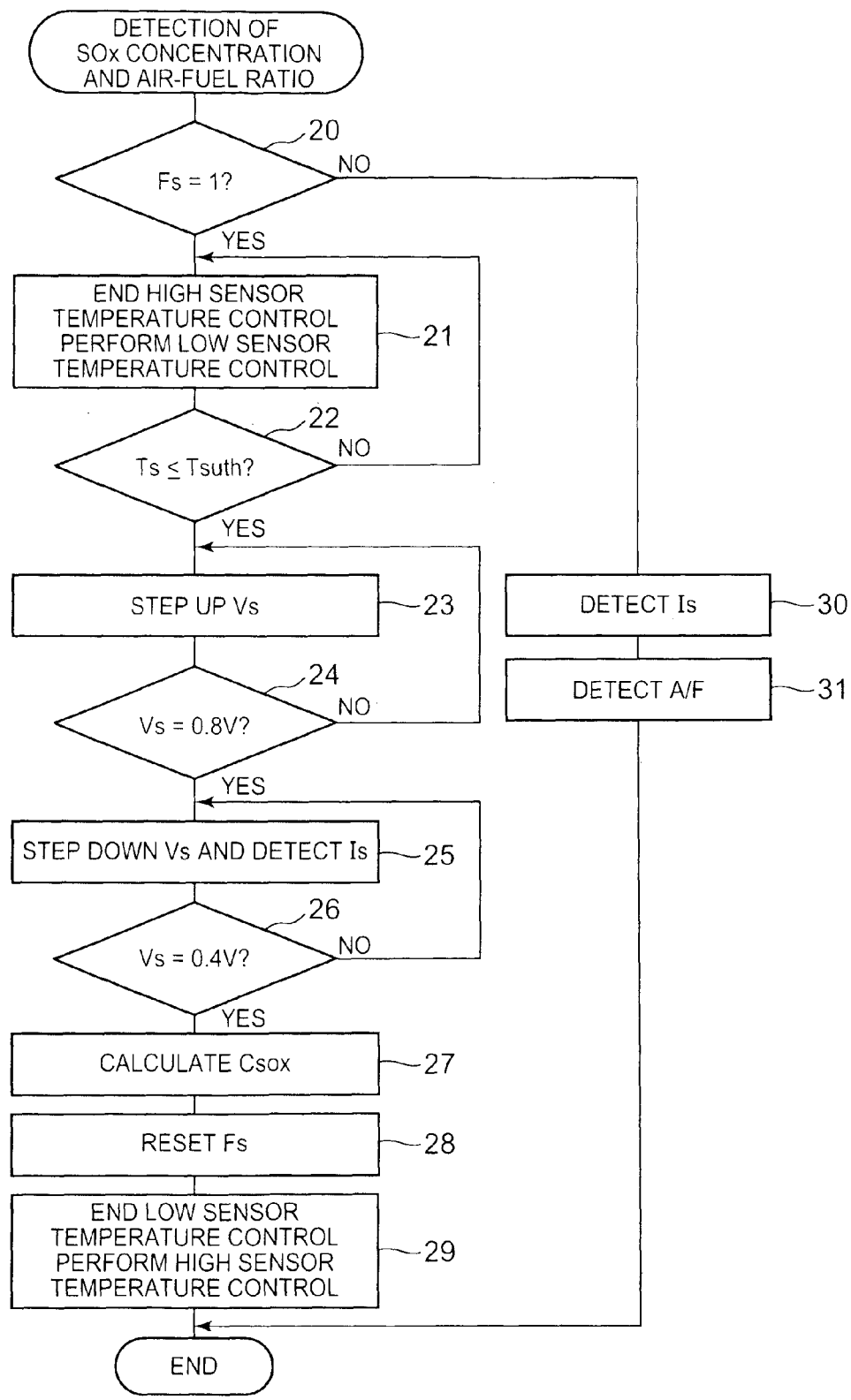
FIG. 12 is a flowchart illustrating an example of an SOx concentration and air-fuel ratio detecting flow in the third embodiment.

An SOx concentration and air-fuel ratio detecting flow of the third embodiment will be described below. An example of this flow is illustrated in FIG. 12. Steps 23 to 27 in the flow illustrated in FIG. 12 are the same as steps 13 to 17 in FIG. 10 and thus description thereof will not be repeated.

When the flow illustrated in FIG. 12 is started, the applied voltage is kept at 0.4 V. In step 20, it is determined whether or not the SOx concentration detection request flag Fs is set (Fs=1). When it is determined that Fs=1 is established, the flow progresses to step 21. On the other hand, when it is determined that Fs=1 is not established, the flow progresses to step 30.

In step 30, the output current Is is detected. Subsequently, in step 31, the air-fuel ratio A/F is calculated on the basis of the output current Is detected in step 30, and then the flow ends.

In step 21, the high sensor temperature control is ended and a low sensor temperature control is performed. The low sensor temperature control is a control of controlling power supplied to the heater so that the sensor temperature is equal to or lower than the predetermined upper-limit temperature. Subsequently, in step 22, it is determined whether or not the sensor temperature Ts is equal to or lower than the predetermined upper-limit temperature Tsuth (Ts≤Tsuth). When it is determined that Ts≤Tsuth is established, the flow progresses to step 23 and the SOx concentration is detected by performing the processes of steps 23 to 27. On the other hand, when it is determined that Ts≤Tsuth is not established, the flow returns to step 21. Accordingly, the low sensor temperature control is repeatedly performed until it is determined that Ts≤Tsuth is established in step 22.

In step 28, The SOx concentration detection request flag Fs is reset. Subsequently, in step 29, the low sensor temperature control is ended, the high sensor temperature control is performed, and then the flow ends.

The SOx concentration detection of a fourth embodiment will be described below. In the SOx concentration detection, when the sensor temperature is equal to or lower than the predetermined upper-limit temperature, the step-up control is performed. That is, the step-up control is performed on the premise that the sensor temperature is equal to or lower than the predetermined upper-limit temperature.

In the fourth embodiment, the step-up control is performed when the sensor temperature is equal to or lower than the predetermined upper-limit temperature, regardless of whether or not it is necessary to detect the SOx concentration. However, when it is necessary to detect the SOx concentration and the sensor temperature is equal to or lower than the predetermined upper-limit temperature, the step-up control may be performed.

Figure 13:
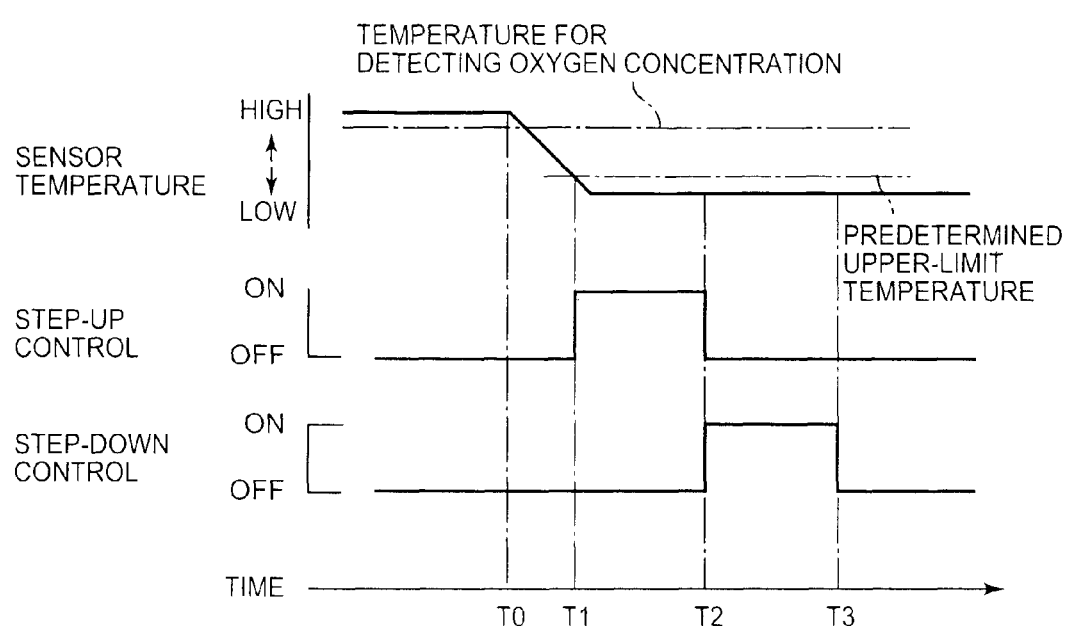
FIG. 13 is a timing chart illustrating a case where an SOx concentration is detected in a fourth embodiment.

The SOx concentration detection of the fourth embodiment will be described below with reference to FIG. 13. In the example illustrated in FIG. 13, prior to time T0, the sensor temperature is equal to or higher than the oxygen concentration detection temperature. At time T0, the sensor temperature starts falling. At time T1, when the sensor temperature is equal to or lower than the predetermined upper-limit temperature, the step-up control is performed. Then, at time T2, the step-down control is performed at the same time as ending the step-up control is ended. At time T3, the step-down control is ended.

According to the SOx concentration detection of the fourth embodiment, for the same reason as described in the first embodiment, it is possible to accurately detect the SOx concentration. According to the SOx concentration detection of the fourth embodiment, the sensor temperature is not actively controlled to be equal to or lower than the predetermined upper-limit temperature so as to detect the SOx concentration. Accordingly, it is possible to more simply and accurately detect the SOx concentration.

Figure 14:
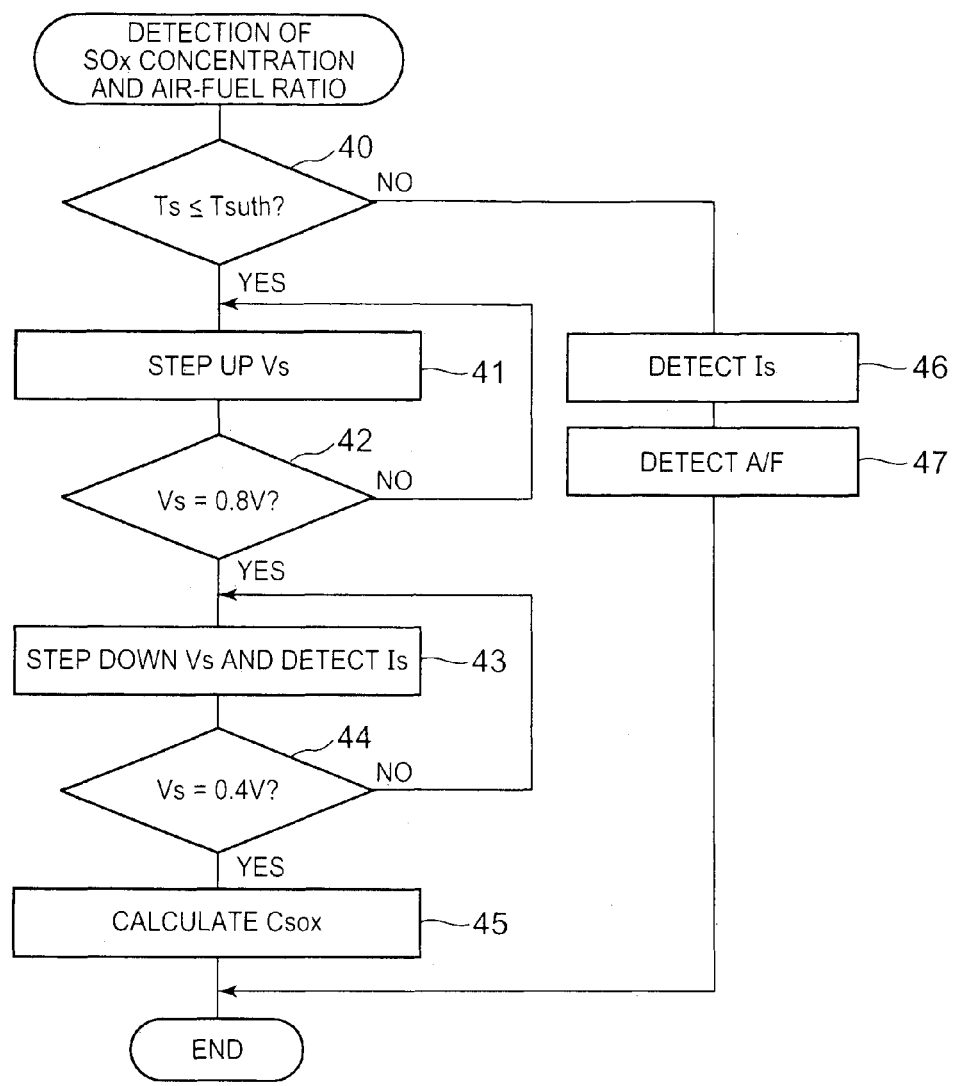
FIG. 14 is a flowchart illustrating an example of an SOx concentration and air-fuel ratio detecting flow in the fourth embodiment.

The SOx concentration and air-fuel ratio detecting flow of the fourth embodiment will be described below. An example of this flow is illustrated in FIG. 14. Steps 41 to 45 and steps 46 to 47 in the flow illustrated in FIG. 14 are the same as steps 23 to 27 and steps 30 to 31 in FIG. 12 and thus description thereof will not be repeated.

When the flow illustrated in FIG. 14 is started, the applied voltage is kept at 0.4 V. Then, in step 40, it is determined whether or not the sensor temperature Ts is equal to or lower than the predetermined upper-limit temperature Tsuth (Ts≤Tsuth). When it is determined that Ts≤Tsuth is established, the flow progresses to step 41 and the SOx concentration Csox is detected by performing the processes of steps 41 to 45. On the other hand, when it is determined that Ts≤Tsuth is not established, the flow progresses to step 46 and the air-fuel ratio A/F is detected by performing the processes of steps 46 to 47.

The SOx concentration detection of a fifth embodiment will be described below. In the SOx concentration detection, when a low temperature condition is established, the step-up control is performed. The low temperature condition is a condition in which the sensor temperature is predicted to be equal to or lower than the predetermined upper-limit temperature.

The low temperature condition is, for example, a condition in which an engine operation (for example, low-load and low-speed operation) in which the exhaust gas temperature is lowered to such an extent as to lower the sensor temperature to be equal to or lower than the predetermined upper-limit temperature is performed. In this case, there is a premise that the sensor temperature is not feedback-controlled to a temperature equal to or higher than the predetermined upper-limit temperature. That is, the premise is that the sensor temperature is executed feed-forward control to a temperature equal to or higher than the predetermined upper-limit temperature.

Alternatively, the low temperature condition is, for example, a condition in which the sensor temperature is controlled to be equal to or lower than the predetermined upper-limit temperature for a purpose other than the step-up control. In this case, the sensor temperature may or may not be feedback-controlled to a temperature equal to or lower than the predetermined upper-limit temperature. In order to effectively achieve the advantages of the fifth embodiment, it is preferable that the sensor temperature be feedback-controlled to a temperature equal to or lower than the predetermined upper-limit temperature.

In the fifth embodiment, regardless of whether or not it is necessary to detect the SOx concentration, the step-up control is performed when the low temperature condition is established. When it is necessary to detect the SOx concentration and the low temperature condition is established, the step-up control may be performed.

In the fifth embodiment, the step-up control is performed regardless of the sensor temperature. The sensor temperature may be detected and the step-up control may be performed after the sensor temperature becomes equal to or lower than the predetermined upper-limit temperature. Alternatively, the step-up control may be performed when the time enough for the sensor temperature to be equal to or lower than the predetermined upper-limit temperature elapses after the low temperature condition is established.

The SOx concentration detection of the fifth embodiment will be described below with reference to FIG. 15. In the following description, Engine Operation I means a normal engine operation in which the sensor temperature is kept equal to or higher than the oxygen concentration detection temperature. Engine Operation II means an engine operation in which the exhaust gas temperature is lowered until the sensor temperature is equal to or lower than the predetermined upper-limit temperature. That is, when Engine Operation II is performed, the low temperature condition is established.

Figure 15:
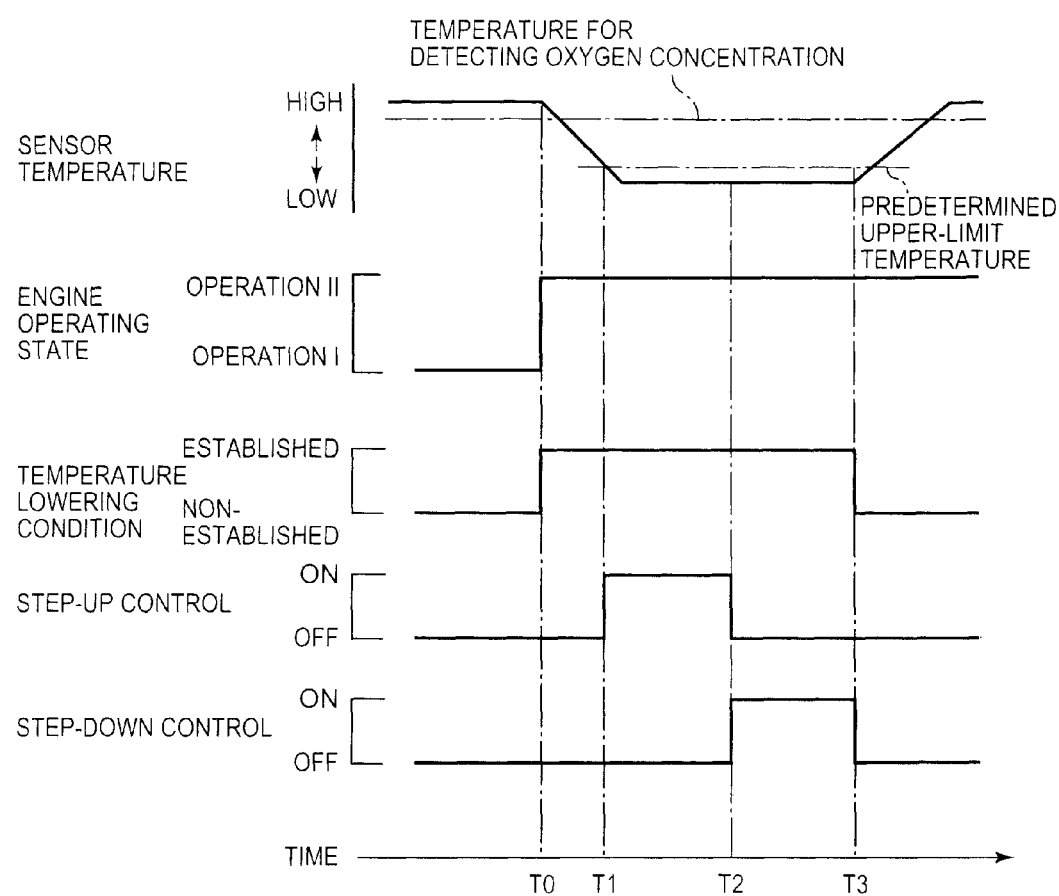
FIG. 15 is a timing chart illustrating a case where an SOx concentration is detected in a fifth embodiment.

In the example illustrated in FIG. 15, prior to time T0, Engine Operation I is performed and the sensor temperature is equal to or higher than the oxygen concentration detection temperature. At time T0, when Engine Operation II is performed, the low temperature condition is established and the sensor temperature starts falling. When the sensor temperature becomes equal to or lower than the predetermined upper-limit temperature at time T1 at which a predetermined time elapses from time T0, the step-up control is performed. At time T2, the step-up control is ended and the step-down control is performed. At time T3, the step-down control is ended.

According to the SOx concentration detection of the fifth embodiment, for the same reason as described in the first embodiment, it is possible to accurately detect the SOx concentration. For the same reason as described in the fourth embodiment, it is possible to further simply and accurately detect the SOx concentration.

Figure 16:
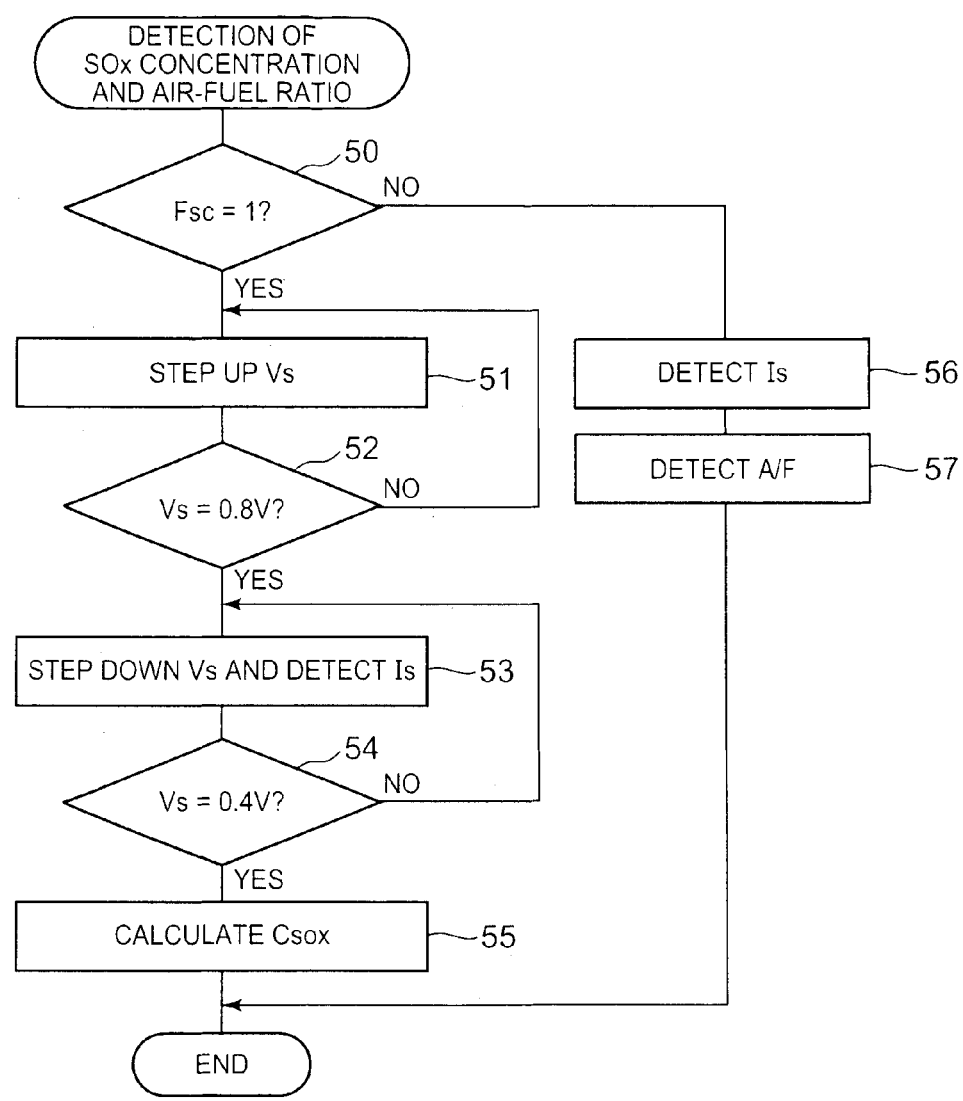
FIG. 16 is a diagram illustrating an example of an SOx concentration and air-fuel ratio detecting flow in the fifth embodiment.

The SOx concentration and air-fuel ratio detecting flow of the fifth embodiment will be described below. An example of this flow is illustrated in FIG. 16. Steps 51 to 55 and steps 56 to 57 in the flow illustrated in FIG. 16 are the same as steps 23 to 27 and steps 30 to 31 in the flow illustrated in FIG. 12 and thus description thereof will not be repeated.

When the flow illustrated in FIG. 16 is started, the applied voltage is kept at 0.4 V. Then, in step 50, it is determined whether or not a low temperature condition establishment flag Fsc is set (Fsc=1). The low temperature condition establishment flag Fsc is set when the low temperature condition is established and is reset when the low temperature condition is not established. When it is determined in step 50 that Fsc=1 is established, the flow progresses to step 51 and the SOx concentration Csox is detected by performing the processes of steps 51 to 55. On the other hand, when it is determined that Fsc=1 is not established, the flow progresses to step 56 and the air-fuel ratio A/F is detected by performing the processes of steps 56 to 57.

The SOx concentration detection of a sixth embodiment will be described below. In the SOx concentration detection, when it is necessary to detect the SOx concentration (that is, when it is necessary to perform the step-up control), the step-up control is performed while performing the exhaust gas temperature lowering control.

In the sixth embodiment, the step-up control is performed regardless of the sensor temperature. The sensor temperature may be detected and the step-up control may be performed after the sensor temperature becomes equal to or lower than the predetermined upper-limit temperature. Alternatively, the step-up control may be performed when the time enough for the sensor temperature to be equal to or lower than the predetermined upper-limit temperature elapses after the exhaust gas temperature lowering control is started.

The sixth embodiment is based on the premise that the sensor temperature is not feedback-controlled to a temperature equal to or higher than the predetermined upper-limit temperature. That is, the sixth embodiment is based on the premise that the sensor temperature is executed feed-forward control to a temperature equal to or higher than the predetermined upper-limit temperature.

According to the SOx concentration detection of the sixth embodiment, for the same reason as described in the first embodiment, it is possible to accurately detect the SOx concentration.

A condition in which the oxygen concentration in the exhaust gas is equal to or higher than a predetermined concentration may be added to the step-up control performance condition in the above-mentioned embodiment. In this case, it is possible to further efficiently and accurately detect the SOx concentration. That is, when the oxygen concentration in the exhaust gas in the step-up control is high, the sulfur component attached to the first sensor electrode in the step-up control is likely to be detached from the first sensor electrode. Therefore, in consideration of the accurate detection of the SOx concentration, it is necessary to suppress the detachment of the sulfur component from the first sensor electrode when the oxygen concentration in the exhaust gas in the step-up control is high. Accordingly, by performing the step-up control only when the oxygen concentration in the exhaust gas is equal to or higher than the predetermined concentration, the step-up control is performed only when it is particularly necessary to suppress the detachment of the sulfur component from the first sensor electrode. As a result, it is possible to further efficiently and accurately detect the SOx concentration.

The SOx concentration detection of a seventh embodiment will be described below. In the seventh embodiment, the SOx concentration detections of the first to sixth embodiments are performed predetermined times and the SOx concentration detected through the SOx concentration detection in which the sensor temperature in the step-up control is the lowest out of the SOx concentration detections is employed as the SOx concentration in the exhaust gas.

As described above, when the sensor temperature excessively low, it is not possible to accurately detect the SOx concentration. However, when the sensor temperature is not excessively low, the lower the sensor temperature becomes, the more accurately the output current in the step-down control corresponds to the SOx concentration. Accordingly, by employing the SOx concentration, which has been detected when the sensor temperature is a lower temperature, as the SOx concentration in the exhaust gas, it is possible to more accurately detect the SOx concentration. Particularly, this idea is useful when the sensor temperature in the step-up control differs whenever the step-up control is performed. Particularly, the ideal is useful for a case where the step-up control is performed when the sensor temperature becomes equal to or lower than the predetermined upper-limit temperature, instead of actively controlling the sensor temperature to be equal to or lower than the predetermined upper-limit temperature.

In an eighth embodiment, the applied voltage is normally kept at 0.4 V. In the SOx concentration detection of the eighth embodiment, the step-up control is performed when one of follows conditions is satisfied, the sensor temperature is equal to or lower than the predetermined upper-limit temperature and the low temperature condition in which the sensor temperature is predicted to be equal to or lower than the predetermined upper-limit temperature is established, and then the step-down control is performed. At this time, the ECU determines whether the absolute value of the peak value of the output current input to the ECU in the step-down control is equal to or greater than an alarm determination value (a first determination value). Here, when the absolute value of the peak value is equal to or greater than the alarm determination value, the ECU gives an alarm notifying that the fuel property is abnormal. In this case, a parameter for determining whether or not it is necessary to give an alarm notifying that the fuel property is abnormal can be said to be calculated as the parameter related to SOx. On the other hand, when the absolute value of the peak value is less than the alarm determination value, the ECU calculates (that is, detects) the SOx concentration using the peak value and the reference current.

The alarm determination value is set, for example, as follows. As described above, the sulfur component of SOx in the exhaust gas may be attached to the first sensor electrode. It has been proved through the study of the inventor et al. of the present invention that the more the attached S amount (that is, the amount of sulfur attached to the first sensor electrode) becomes, the greater the absolute value of the peak value becomes. When the attached S amount is very large, there is a possibility that the detection accuracy (particularly, the SOx concentration detection accuracy) of the limiting current sensor will be lowered. Here, one reason for the increase in the attached S amount is that the SOx concentration in the exhaust gas is high. When the sulfur component concentration in the fuel is high, the SOx concentration in the exhaust gas is high. When the sulfur component concentration in the fuel is high so as not to be allowable and thus there is a possibility that the fuel property is abnormal, it is preferable that the intent be alarmed.

Therefore, the alarm determination value is set to a value which is appropriately selected to be equal to or greater than the minimum value of the absolute value of the peak value (that is, the absolute value of the peak value of the output current input to the ECU in the step-down control), for example, when the fuel property is not a property within an allowable range (particularly, when the S concentration in the fuel is higher than the allowable concentration).

According to the SOx concentration detection of the eighth embodiment, when there is a possibility that the fuel property is abnormal, the intent thereof is alarmed and it is thus possible to give an alarm notifying that there is a possibility that the fuel property is abnormal.

Figure 17:
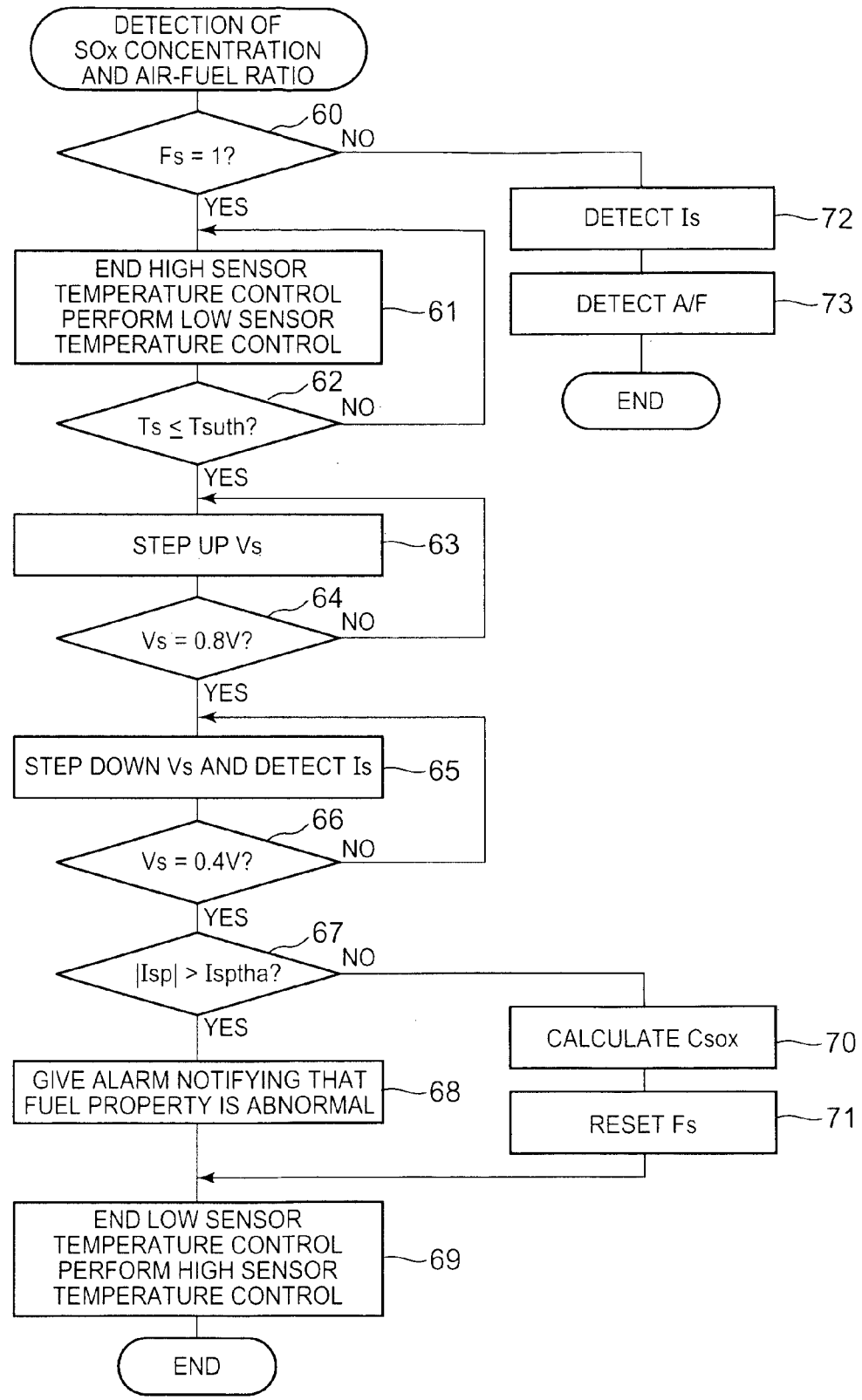
FIG. 17 is a flowchart illustrating an example of an SOx concentration and air-fuel ratio detecting flow in an eighth embodiment.

The SOx concentration and air-fuel ratio detecting flow of the eighth embodiment will be described below. An example of this flow is illustrated in FIG. 17. Steps 60 to 66 and steps 72 to 73 of the flow illustrated in FIG. 17 are the same as steps 20 to 26 and steps 30 to 31 of the flow illustrated in FIG. 12, respectively, and thus description thereof will not be repeated.

In step 67 of the flow of FIG. 17, it is determined whether the absolute value Iisp of the peak value of the output current Is detected in step 65 is greater than the alarm determination value Isptha (|Isp|>Isptha). Here, when it is determined that |Isp|>Isptha is established, the flow progresses to step 68, the alarm notifying that the fuel property is abnormal is given, and then the flow progresses to step 69. On the other hand, when it is determined that |Isp|>Isptha is not established, the flow progresses to step 70 and the SOx concentration Csox is calculated on the basis of the peak value of the output current Is detected in step 65. Subsequently, in step 71, the SOx concentration detection request flag Fs is reset and then the flow progresses to step 69. In step 69, the low sensor temperature control is ended, the high sensor temperature control is performed, and then the flow ends.

In the SOx concentration detection of a ninth embodiment, similarly to the eighth embodiment, the step-up control is first performed and then the step-down control is performed. At this time, the ECU determines whether the absolute value of the peak value of the output current input to the ECU in the step-down control is equal to or greater than a sulfur poisoning reducing determination value. When the absolute value of the peak value is equal to or greater than the sulfur poisoning reducing determination value, the ECU performs a sulfur poisoning reducing control. In this case, a parameter for determining whether it is necessary to perform the sulfur poisoning reducing control can be said to be calculated as the parameter related on SOx. On the other hand, when the absolute value of the peak value is less than the sulfur poisoning reducing determination value, the ECU calculates (that is, detects) the SOx concentration using the peak value and the reference current.

The sulfur poisoning reducing determination value is set, for example, as follows. As described in the eighth embodiment, when the attached S amount is very large, the detection accuracy (particularly, the SOx concentration detection accuracy) of the limiting current sensor may be lowered. Therefore, when the attached S amount is large, it is preferable that sulfur attached to the first sensor electrode be removed (that is, the sulfur poisoning reducing control be performed). Accordingly, the sulfur poisoning reducing determination value is set to the absolute value of the peak value (that is, the absolute value of the peak value of the output current input to the ECU in the step-down control), for example, when it is necessary to perform the sulfur poisoning reducing control.

The sulfur poisoning reducing determination value may be a value equal to or different from the alarm determination value in the eighth embodiment.

According to the SOx concentration detect of the ninth embodiment, when there is a possibility that the detection accuracy of the sensor is lowered due to sulfur poisoning, the sulfur poisoning reducing control is performed. In other words, it is possible to detect the SOx concentration only when there is no possibility that the detection accuracy of the sensor is lowered due to the sulfur poisoning. Accordingly, according to the SOx concentration detector according to the ninth embodiment, it is possible to further accurately detect the SOx concentration.

The sulfur poisoning reducing control will be described below. This control is a control for reducing the sulfur poisoning of the limiting current sensor 10 or 30. The sulfur poisoning means degradation of the limiting current sensor 10 or 30 (more specifically, the first sensor electrode 16A or 35A) due to SOx in the exhaust gas.

In the above-mentioned embodiment, the applied voltage is normally kept at 0.4 V. That is, 0.4 V is normally applied to the sensor. When it is necessary to reduce the sulfur poisoning, the applied voltage increases from 0.4 V to 0.8 V and then the applied voltage decreases from 0.8 V to 0.4 V. Accordingly, the sulfur poisoning of the sensor is reduced and the sulfur poisoning of the sensor is reduced as a result by repeating the control.

The one-cell limiting current sensor can be used to detect an NOx concentration in the exhaust gas. In this case, a voltage is applied to the pump cell so that the oxygen concentration in the exhaust gas is substantially zero by the pumping of the pump cell, and a voltage is applied to the sensor cell so that NOx in the exhaust gas is decomposed in the sensor cell and a current flows in the sensor cell by oxygen in the NOx. At this time, it is possible to detect the NOx concentration in the exhaust gas on the basis of the output current of the sensor (specifically, the output current of the sensor cell).

Figure 18A:
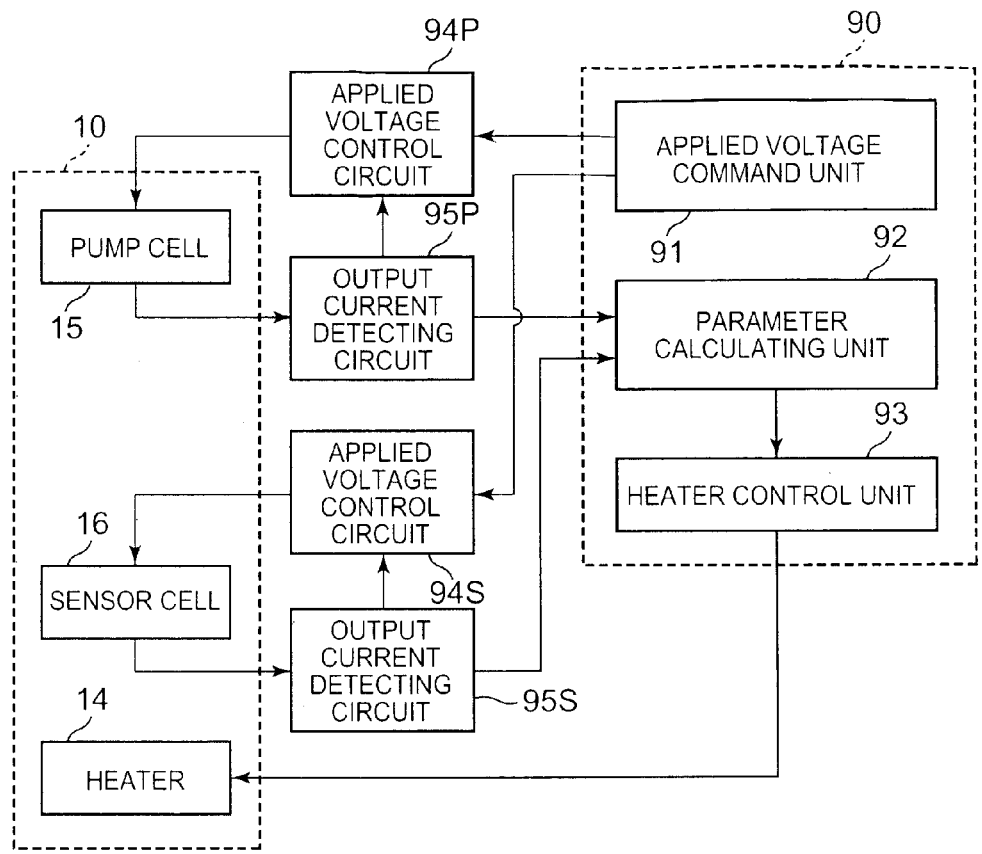
FIG. 18A is a diagram illustrating an example of a circuit employed by the limiting current sensor illustrated in FIG. 1.

When the internal combustion engine includes the limiting current sensor (two-cell limiting current sensor) illustrated in FIG. 1, a circuit illustrated in FIG. 18A is employed as an SOx detecting circuit. In FIG. 18A, reference numeral 10 denotes a limiting current sensor (that is, the limiting current sensor illustrated in FIG. 1), 14 denotes a heater, 15 denotes a pump cell, 16 denotes a sensor cell, 90 denotes an ECU, 91 denotes an applied voltage command unit, 92 denotes a parameter calculating unit, 93 denotes a heater control unit, 94P and 94S denote applied voltage control circuits, and 95P and 95S denote output current detecting circuits.

The applied voltage command unit 91, the parameter calculating unit 92, and the heater control unit 93 are elements of the ECU 90.

The applied voltage command unit 91 transmits a command relevant to the applied voltage to the pump cell 15 to the applied voltage control circuit 94P and transmits a command relevant to the applied voltage to the sensor cell 16 to the applied voltage control circuit 94S.

The parameter calculating unit 92 receives a signal corresponding to a pump cell output current from the output current detecting circuit 95P and calculates the pump cell output current on the basis of the received signal. The parameter calculating unit 92 calculates the air-fuel ratio of the exhaust gas (or the oxygen concentration in the exhaust gas) on the basis of the calculated output current. The parameter calculating unit 92 receives a signal corresponding to the sensor cell output current from the output current detecting circuit 95S and calculates the sensor cell output current on the basis of the received signal. The parameter calculating unit 92 calculates the SOx concentration in the exhaust gas on the basis of the calculated output current. The parameter calculating unit 92 calculates impedance of circuits in the limiting current sensor 10 on the basis of the signal received from the output current detecting circuits 95P, 95S, and transmits information on the calculated impedance to the heater control unit 93. The heater control unit 93 transmits a control signal for controlling the heater 14 on the basis of the information on the impedance received from the parameter calculating unit 92 to the heater 14.

The applied voltage control circuit 94P controls the pump cell application voltage on the basis of the command received from the applied voltage command unit 91. Alternatively, the applied voltage control circuit controls the pump cell application voltage on the basis of the command received from the applied voltage command unit 91 and the signal corresponding to the pump cell output current supplied from the output current detecting circuit 95P.

The output current detecting circuit 95P detects the pump cell output current and transmits a signal corresponding to the detected pump cell output current to the parameter calculating unit 92 and the applied voltage control circuit 94P.

The applied voltage control circuit 94S controls the sensor cell application voltage on the basis of the command received from the applied voltage command unit 91. Alternatively, the applied voltage control circuit controls the sensor cell application voltage on the basis of the command received from the applied voltage command unit 91 and the signal corresponding to the sensor cell output current supplied from the output current detecting circuit 95S.

The output current detecting circuit 95S detects the sensor cell output current and transmits a signal corresponding to the detected sensor cell output current to the parameter calculating unit 92 and the applied voltage control circuit 94S.

Figure 18B:
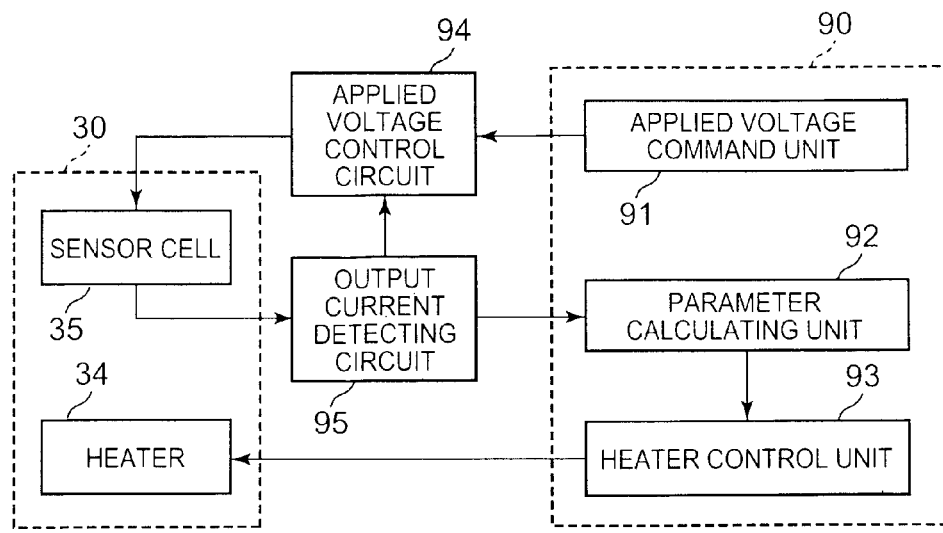
FIG. 18B is a diagram illustrating an example of a circuit employed by the limiting current sensor illustrated in FIG. 5.

When the internal combustion engine includes the limiting current sensor (one-cell limiting current sensor) illustrated in FIG. 5, a circuit illustrated in FIG. 18B is employed as an SOx detecting circuit. In FIG. 18B, reference numeral 30 denotes a limiting current sensor (that is, the limiting current sensor illustrated in FIG. 5), reference numeral 34 denotes a heater, reference numeral 35 denotes a sensor cell, reference numeral 90 denotes an ECU, reference numeral 91 denotes an applied voltage command unit, reference numeral 92 denotes a parameter calculating unit, reference numeral 93 denotes a heater control unit, reference numeral 94 denotes an applied voltage control circuit, and reference numeral 95 denotes an output current detecting circuit.

The applied voltage command unit 91, the parameter calculating unit 92, and the heater control unit 93 are elements of the ECU 90.

The applied voltage command unit 91 transmits a command relevant to the applied voltage to the sensor cell 35 to the applied voltage control circuit 94.

The parameter calculating unit 92 receives a signal corresponding to a sensor cell output current from the output current detecting circuit 95 and calculates the sensor cell output current on the basis of the received signal. The parameter calculating unit 92 calculates the air-fuel ratio of the exhaust gas (or the oxygen concentration in the exhaust gas) or the SOx concentration in the exhaust gas on the basis of the calculated output current. The parameter calculating unit 92 calculates impedance of circuits in the sensor 30 on the basis of the signal received from the output current detecting circuit 95, and transmits information on the calculated impedance to the heater control unit 93. The heater control unit 93 transmits a control signal for controlling the heater 34 on the basis of the information on the impedance received from the parameter calculating unit 92 to the heater 34.

The applied voltage control circuit 94 controls the sensor cell application voltage on the basis of the command received from the applied voltage command unit 91. Alternatively, the applied voltage control circuit controls the sensor cell application voltage on the basis of the command received from the applied voltage command unit 91 and the signal corresponding to the sensor cell output current supplied from the output current detecting circuit 95.

The output current detecting circuit 95 detects the sensor cell output current and transmits a signal corresponding to the detected sensor cell output current to the parameter calculating unit 92 and the applied voltage control circuit 94.

When a catalyst for purifying components of the exhaust gas is provided to the exhaust pipe, there is a possibility that SOx in the exhaust gas will be captured by the catalyst. In this case, when the limiting current sensor is attached to the exhaust pipe downstream from the catalyst, there is a possibility that the SOx concentration will not be accurately detected. Accordingly, in the above-mentioned embodiment, when the exhaust pipe is provided with the catalyst, it is preferable that the limiting current sensor be attached to the exhaust pipe upstream from the catalyst.

In the SOx concentration detection of the above-mentioned embodiment, it is considered that the reason of outputting the current corresponding to the SOx concentration from the sensor when the applied voltage decreases is that a reaction associated with SOx occurs in the sensor cell. On the other hand, this reaction is greatly affected by the temperature of the sensor cell. Therefore, in consideration of the fact that the SOx concentration in the exhaust gas is very low, it is preferable that the temperature of the sensor cell be kept constant. Accordingly, in the above-mentioned embodiment, the heater may be controlled so as to keep the temperature of the sensor cell constant at the time of detecting the SOx concentration. As a result, it is possible to further accurately detect the SOx concentration.

It is preferable that the SOx concentration detection of the above-mentioned embodiment be performed just after fuel feed (supplement of the fuel tank with a fuel to be supplied to the fuel injection valve) is carried out or at the earliest time thereafter.

The above-mentioned embodiment is an embodiment in which the SOx concentration in the exhaust gas is detected. The idea of the above-mentioned embodiment can be applied to a case where a parameter related to SOx having a correlation with the output current when the applied voltage decreases from, the predetermined voltage is calculated. Examples of the SOx-relevant parameter include a coefficient that is used to control the internal combustion engine and that is set depending on the amount of SOx. This case is based on the premise that the output current having a correlation with the SOx-relevant parameter to be detected can be separated from the other output current having a correlation with the SOx-relevant parameter.

In other words, the idea of the above-mentioned embodiment is that the SOx-relevant parameter has no correlation with the output current when the applied voltage is kept at a constant voltage (or a very small correlation) or has no correlation with the output current when the applied voltage increases (or a very small correlation), but can be applied to a case where the SOx-relevant parameter having a correlation with the output current when the applied voltage decreases from a predetermined voltage is calculated.

The above-mentioned embodiment is an embodiment in which the SOx concentration is detected using the minimum value of the output current in the step-down control. The idea of the above-mentioned embodiments can be applied to even a case where the parameter related to SOx is calculated using the maximum value of the output current in the step-down control.

In the embodiment in which the sensor is used to detect the SOx concentration and the air-fuel ratio out of the above-mentioned embodiments, the sensor may be used to detect only the SOx concentration.

The control device according to the above-mentioned embodiment is a control device for an internal combustion engine including a limiting current sensor (for example, the limiting current sensor 10, 30) and is a control device that calculates the parameter (for example, SOx concentration) related to SOx in the target gas (for example, exhaust gas) using the output current of the sensor when the step-down control of stepping down the voltage applied to the sensor from the parameter calculation voltage (a predetermined voltage, for example, 0.8 V) is performed. The control device according to the above-mentioned embodiment is a control device including a control unit (for example, ECU 90) that performs the step-up control of stepping up the applied voltage to the parameter calculation voltage when the temperature of the sensor is equal to or lower than the predetermined upper-limit temperature (for example, equal to or lower than 700° C.) or when the low temperature condition in which the temperature of the sensor is predicted to be equal to or lower than the predetermined upper-limit temperature is established.

What is claimed is:

1. A control device for an internal combustion engine including a limiting current sensor, the control device comprising:
an electronic controller configured to:
(a) step up a voltage applied to a sensor cell of the limiting current sensor to a predetermined voltage so that the sensor cell of the limiting current sensor is warmed up when one of following conditions is satisfied,
(i) a temperature of the limiting current sensor is equal to or lower than a first predetermined temperature, and
(ii) a condition in which the temperature of the limiting current sensor is predicted to be equal to or lower than the first predetermined temperature is established,
wherein
a sulfur component in SOx is attached to a first sensor electrode of the sensor cell of the limiting current sensor when the voltage applied to the limiting current sensor increases,
the sulfur component in SOx is detached from the first sensor electrode of the sensor cell of the limiting current sensor when stepping down the voltage applied to the sensor cell of the limiting current sensor; and
(b) calculate a parameter related to SOx in a target gas based on a peak value of an output current from the sensor cell of the limiting current sensor which is input to the electronic controller when the voltage applied to the sensor cell of the limiting current sensor is stepped down from the predetermined voltage, and a reference current.

2. The control device according to claim 1, wherein the electronic controller is configured to control such that one of the conditions is satisfied, in the course of warming the limiting current sensor up.

3. The control device according to claim 1, wherein the electronic controller is configured to give an alarm notifying that a fuel property is abnormal when an absolute value of the output current while stepping down the voltage applied to the limiting current sensor from the predetermined voltage is equal to or greater than a first determination value.

4. The control device according to claim 1, wherein the electronic controller is configured to step up the voltage applied to the limiting current sensor to the predetermined voltage when the temperature of the limiting current sensor is equal to or higher than a second predetermined temperature and is equal to or lower than the first predetermined temperature, the second predetermined temperature is lower than the first predetermined temperature.

5. The control device according to claim 1, wherein the electronic controller is configured to step up the voltage applied to the limiting current sensor to the predetermined voltage when an oxygen concentration in the target gas is equal to or higher than a predetermined concentration.

6. The control device according to claim 1, wherein the electronic controller is configured to step up the voltage applied to the limiting current sensor to the predetermined voltage after a process of reducing sulfur poisoning of the limiting current sensor ends.

7. The control device according to claim 1, wherein the limiting current sensor is configured to detect an oxygen concentration in the target gas, and
the first predetermined temperature is set to a temperature lower than a lower-limit temperature of the limiting current sensor suitable for detecting the oxygen concentration by the use of the limiting current sensor when the electronic controller steps up the voltage applied to the limiting current sensor to the predetermined voltage.

8. The control device according to claim 1, wherein when a plurality of the parameters are calculated, the electronic controller is configured to set the parameter calculated when the temperature of the limiting current sensor is a lower temperature as a final parameter related to SOx.

9. The control device according to claim 1, wherein the predetermined voltage is equal to or higher than 0.8 V.

10. The control device according to claim 1, wherein the applied voltage at the time of ending of stepping down the voltage applied to the limiting current sensor from the predetermined voltage is equal to or lower than 0.7 V.

11. The control device according to claim 1, wherein the electronic controller is configured to apply a second voltage lower than the predetermined voltage to the limiting current sensor, and
he electronic controller is configured to detect an oxygen concentration in the target gas using the output current of the limiting current sensor when the second voltage is applied to the limiting current sensor.

12. A control method for an internal combustion engine including a limiting current sensor and an electronic controller, the control method comprising:
(a) stepping up, by the electronic controller, a voltage applied to a sensor cell of the limiting current sensor to a predetermined voltage so that the sensor cell of the limiting current sensor is warmed up when one of following conditions is satisfied,
(i) a temperature of the limiting current sensor is equal to or lower than a first predetermined temperature, and
(ii) a condition in which the temperature of the limiting current sensor is predicted to be equal to or lower than the first predetermined temperature is established; wherein
a sulfur component in SOx is attached to a first sensor electrode of the sensor cell of the limiting current sensor when the voltage applied to the limiting current sensor increases,
the sulfur component in SOx is detached from the first sensor electrode of the sensor cell of the limiting current sensor when stepping down the voltage applied to the sensor cell of the limiting current sensor, and
(b) calculating, by the electronic controller, a parameter related to SOx in a target gas based on a peak value of an output current from the sensor cell of the limiting current sensor which is input to the electronic controller when the voltage applied to the sensor cell of the limiting current sensor is stepped down from the predetermined voltage, and a reference current.

* * * * *